United States Patent
Carter et al.

(10) Patent No.: US 6,554,781 B1
(45) Date of Patent: Apr. 29, 2003

(54) SPINAL MONITOR APPARATUS AND METHOD

(75) Inventors: Michael Anthony Carter, Mansfield (AU); Gwendolen Anne Jull, The Gap (AU); Carolyn Anne Richardson, Mooloolaba (AU); Christine Hamilton, Erlangen (DE); Suzanne Louise Roll, St. Lucia (AU); Robert Stephen Matchett, Mosman (AU); Peter Wilson Hill, Redfern (AU); David John Bull, Marsfield (AU); Bradley Peter Ryan, Corinda (AU); Geoffrey David Sizer, Turramurra (AU); Paul Moutzouris, Ryde (AU)

(73) Assignees: Spinal Sensor Technologies Limited, Christchurch (NZ); Carter (New Zealand) Limited, Christchurch (NZ)

(*) Notice: Subject to any disclaimer, the term of this patent is extended or adjusted under 35 U.S.C. 154(b) by 0 days.

(21) Appl. No.: 09/622,294
(22) PCT Filed: Dec. 14, 1999
(86) PCT No.: PCT/AU99/01116
§ 371 (c)(1), (2), (4) Date: Nov. 7, 2000
(87) PCT Pub. No.: WO00/35345
PCT Pub. Date: Jun. 22, 2000

(30) Foreign Application Priority Data

Dec. 14, 1998 (AU) .............................. PP 7678

(51) Int. Cl.$^7$ ............................................ A61B 5/103
(52) U.S. Cl. ................................................. 600/594
(58) Field of Search ................................... 600/594

(56) References Cited

U.S. PATENT DOCUMENTS

| | | | |
|---|---|---|---|
| 3,991,745 A | * 11/1976 | Yoslow et al. | 600/594 |
| 4,730,625 A | 3/1988 | Fraser et al. | 128/781 |
| 5,082,002 A | * 1/1992 | Silverman et al. | 600/594 |
| 5,755,647 A | * 5/1998 | Watnik | 482/121 |

FOREIGN PATENT DOCUMENTS

| | | | |
|---|---|---|---|
| DE | 8605103 | 11/1986 | A61B/5/10 |
| DE | 4205790 | 2/1992 | A61B/5/103 |
| FR | 2715821 | 8/1995 | A61B/5/11 |
| WO | WO 91/06082 | 5/1991 | G08B/21/00 |

* cited by examiner

Primary Examiner—Max F. Hindenburg
Assistant Examiner—Pamela L Wingood
(74) Attorney, Agent, or Firm—Heslin Rothenberg Farley & Mesiti P.C.

(57) ABSTRACT

A method and apparatus for monitoring posture deficiencies in the spine and including a flexible body (30) encapsulating a flexible operating arm (31) cantilevered from a base moulding (34). The operating arm (31) is provided with upper (37) and lower (40) strain gauges bonded to the upper and lower faces respectively of the operating arm (31) at the point beyond the stiffening base moulding (34) to ensure that differential strain is experienced on deflection of the operating arm (31). Wire tails (41) are terminated as a PCB assembly (45) mounted to the printed circuit support (35), which assembly comprises a PC board bearing an LSI processor (46), rechargeable battery (47), vibrating motor (50) and inductive coil (51) selected to fulfil the functions of transmitting and receiving element, and inductive power supply for charging the battery (47), under the control of processor (46). The base moulding (34) is intended to be located in the region of L4 and L5, the flexible body (30) and base moulding (34) being secured in place by surgical adhesive.

25 Claims, 28 Drawing Sheets

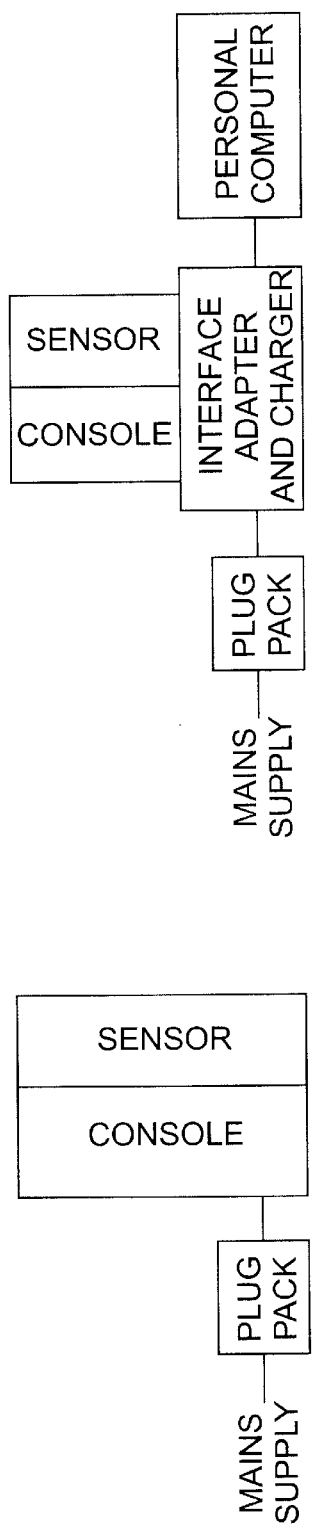
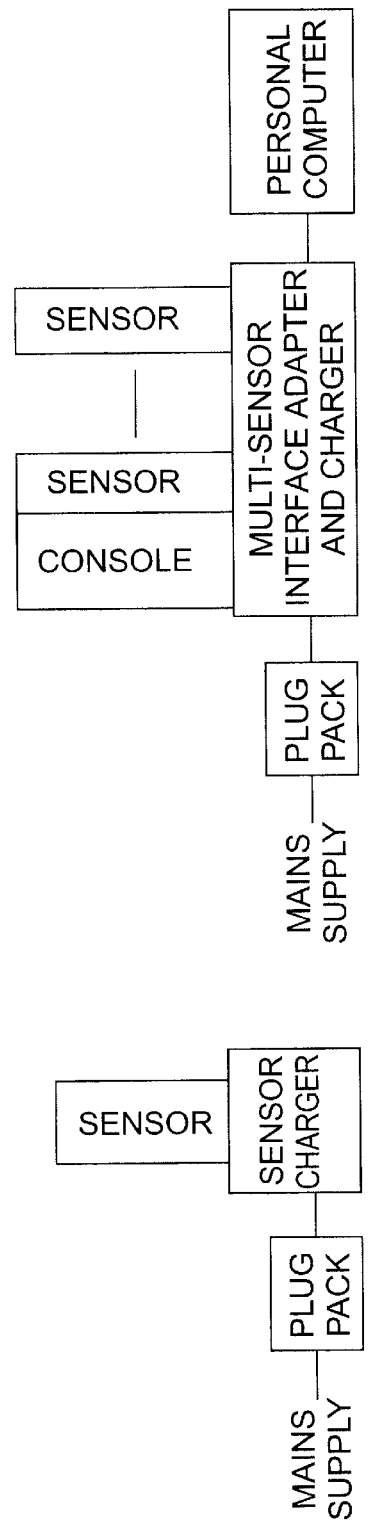
FIG. 5

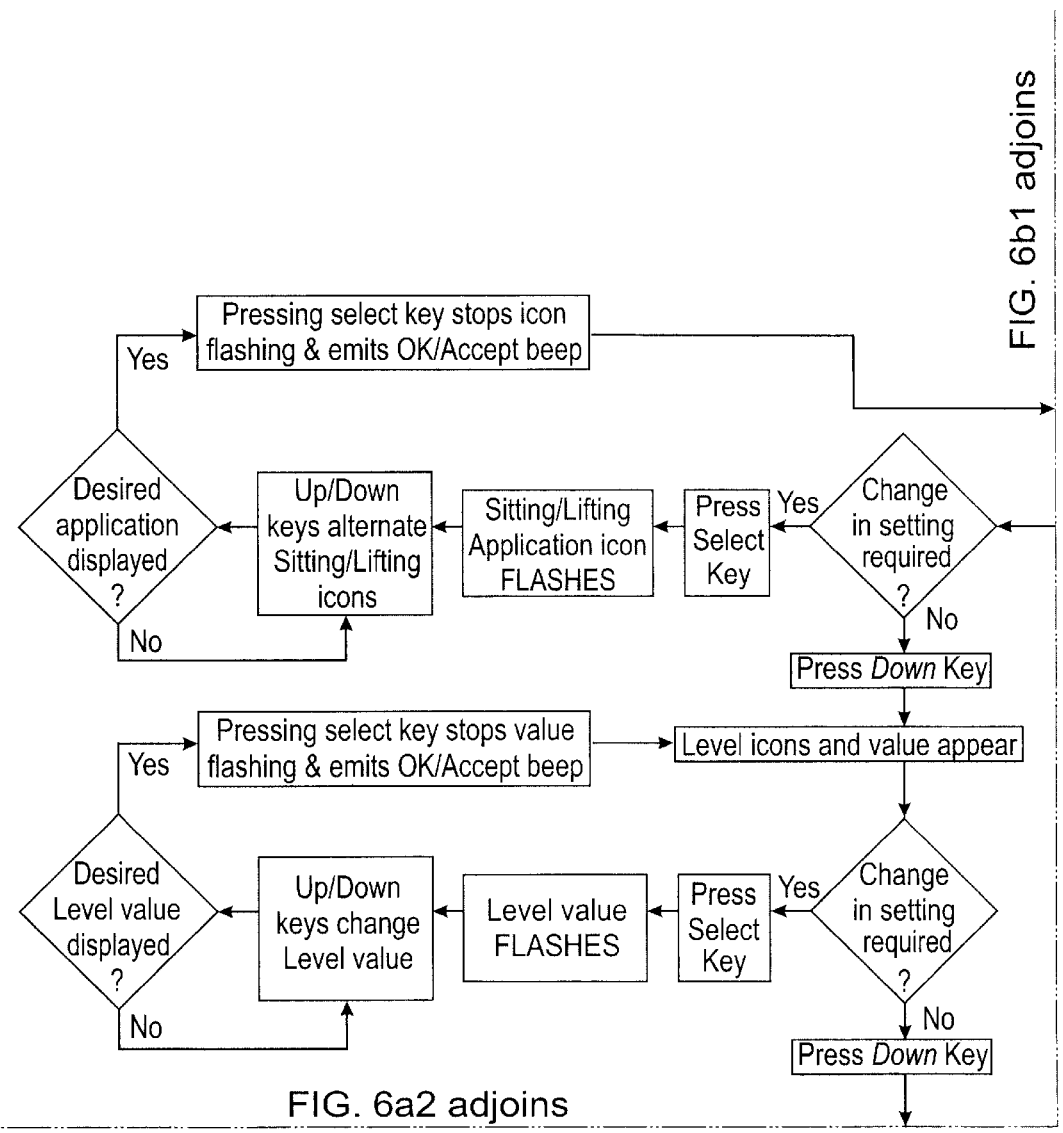
FIG. 6a1

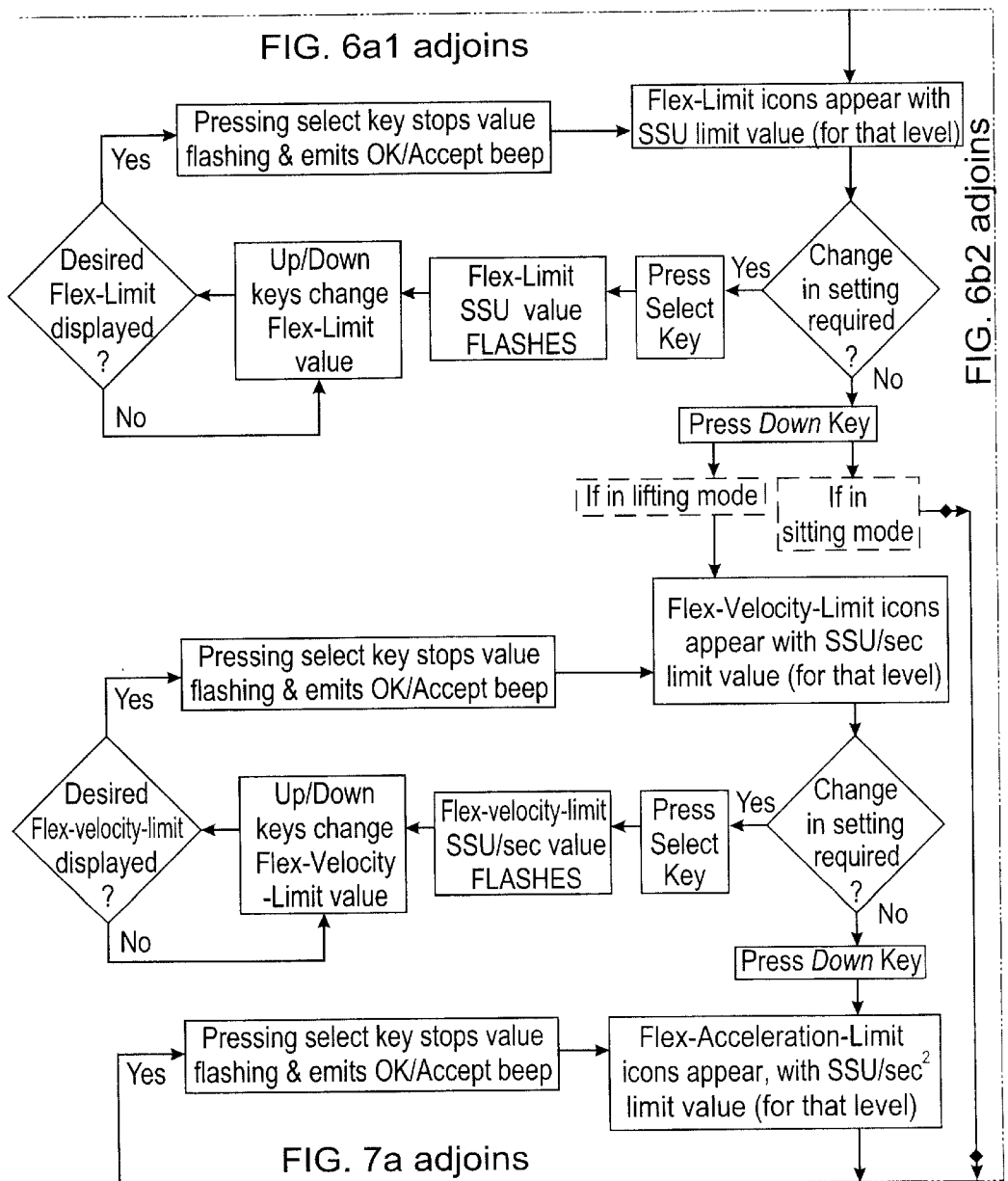
FIG. 6a2

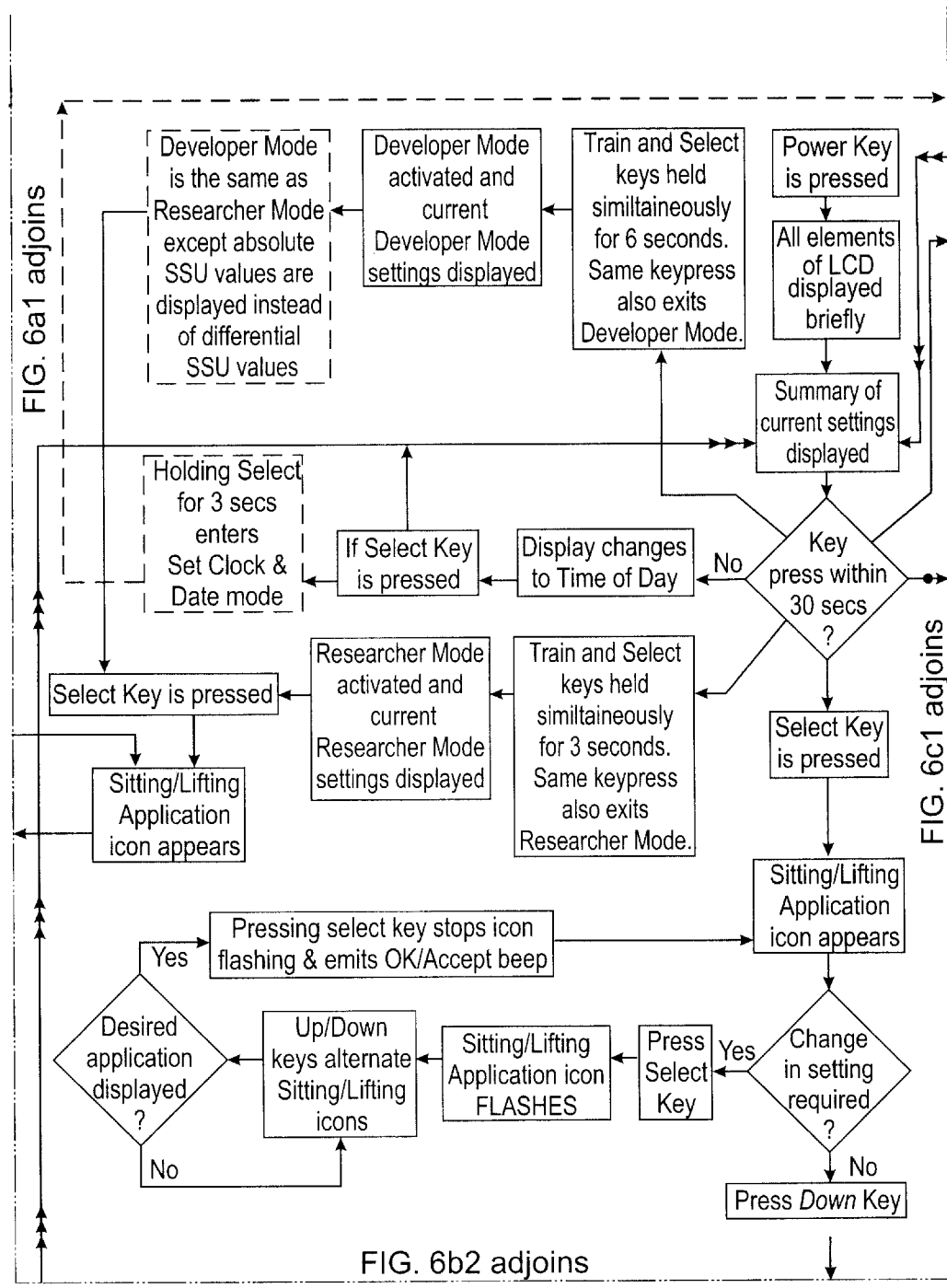
FIG. 6b1

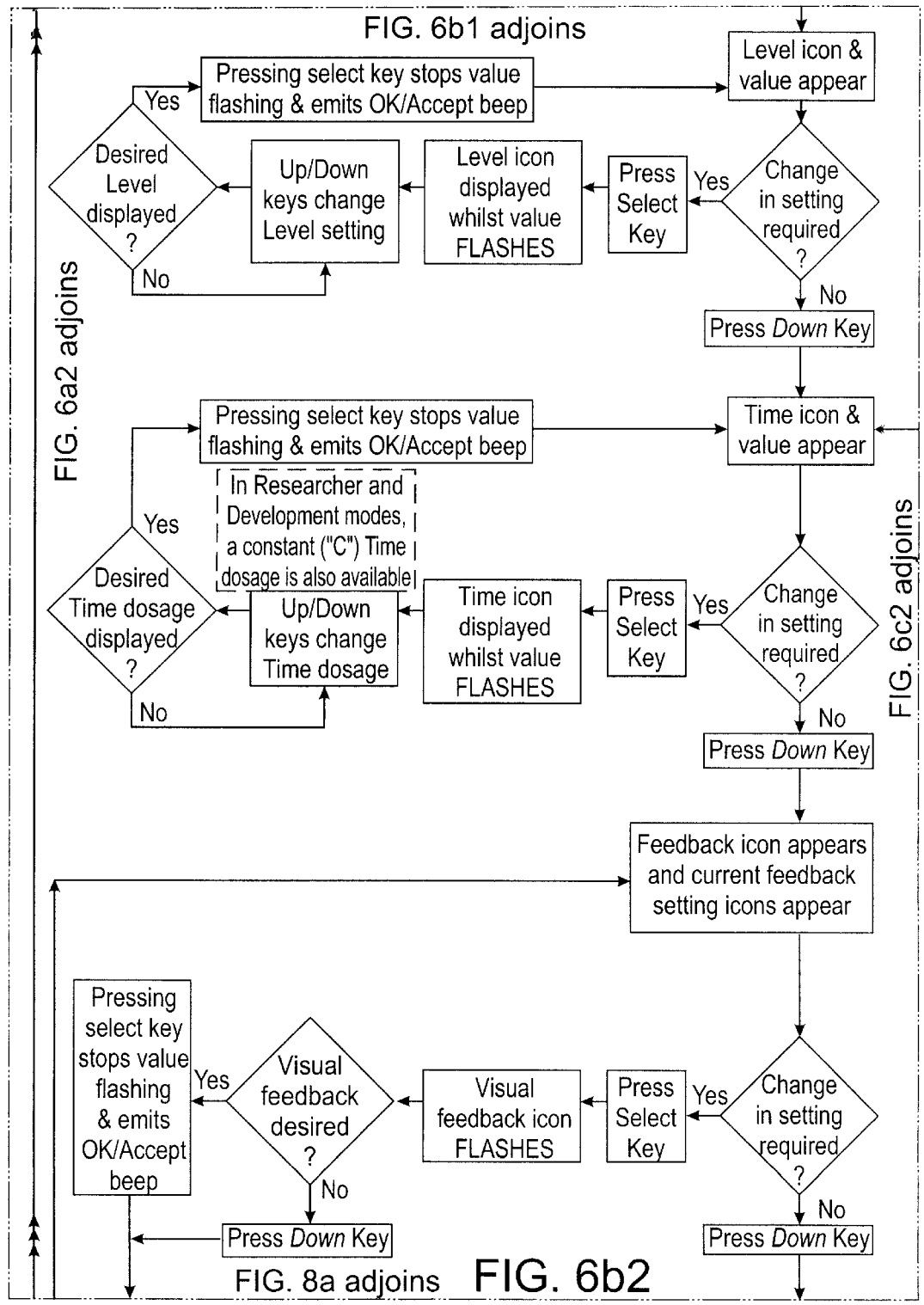
FIG. 6b2

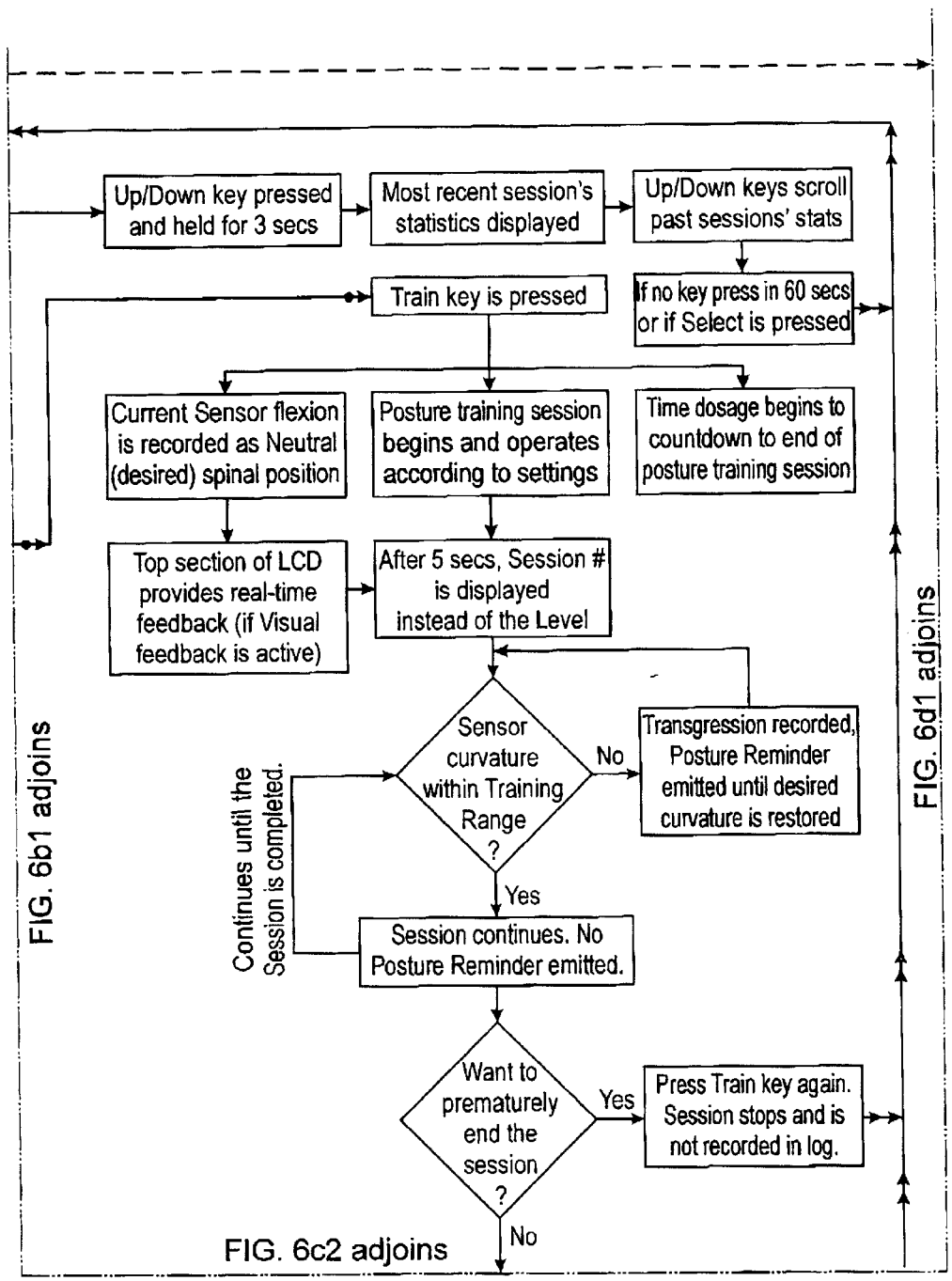
FIG. 6c1

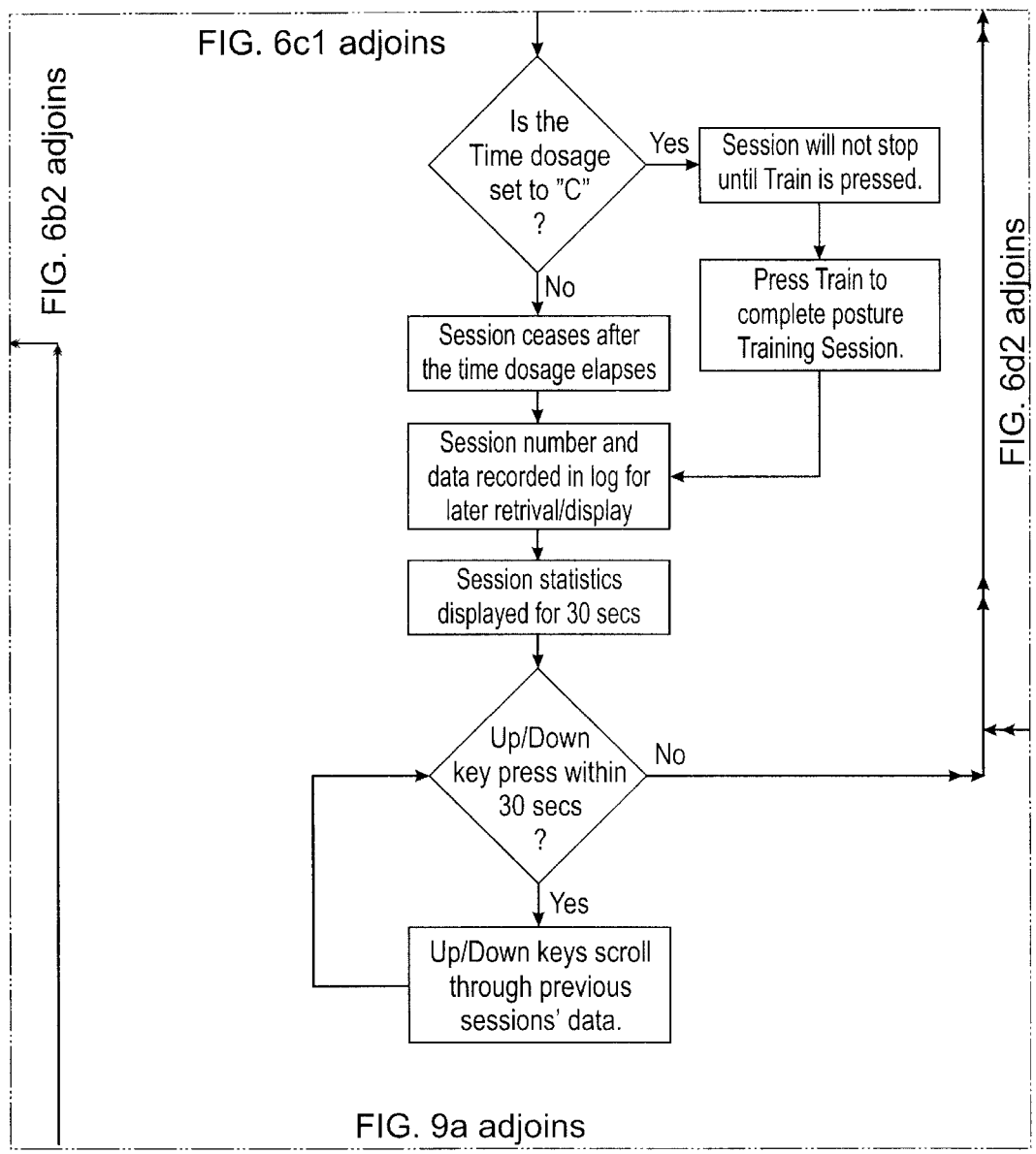
FIG. 6c2

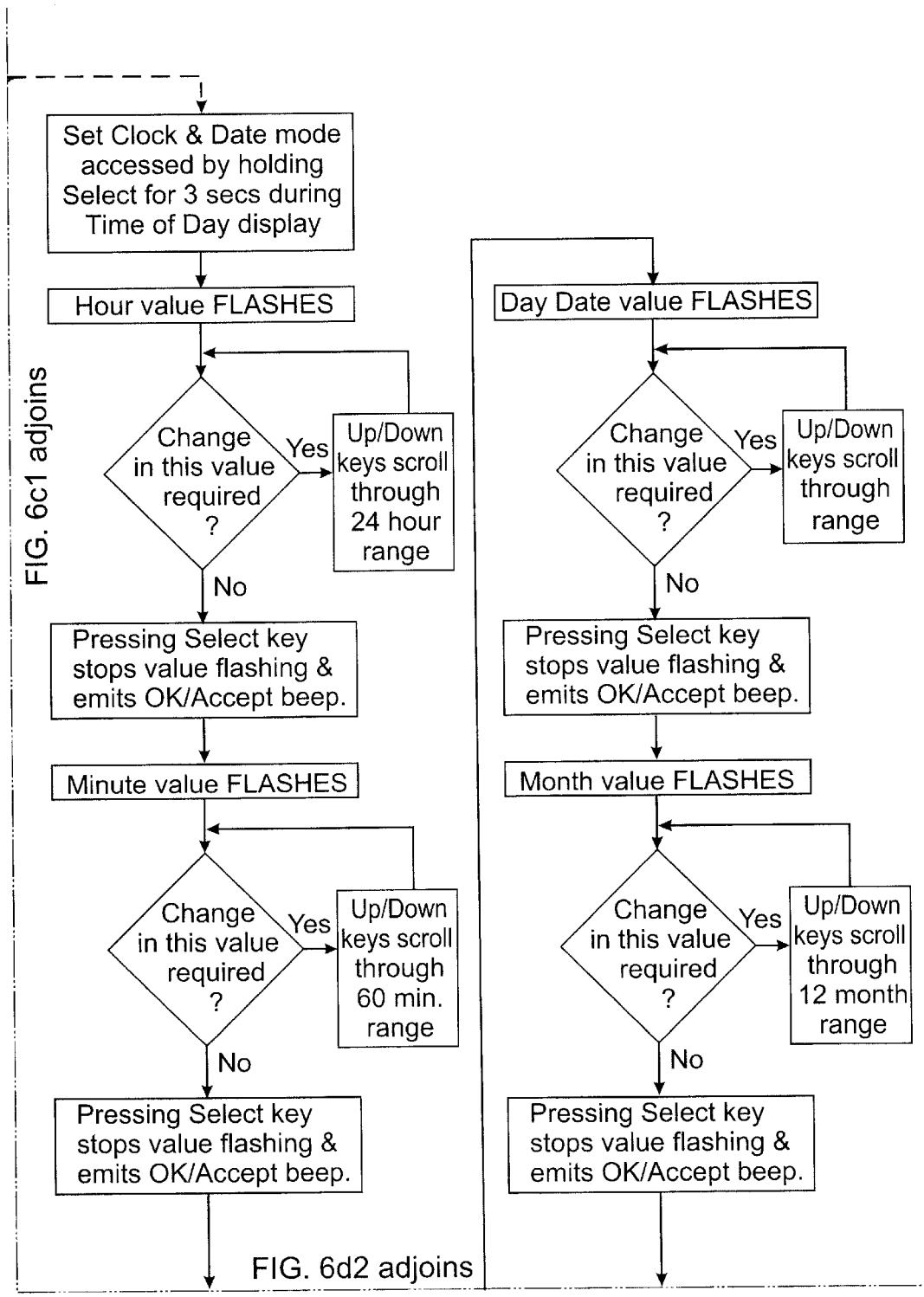
FIG. 6d1

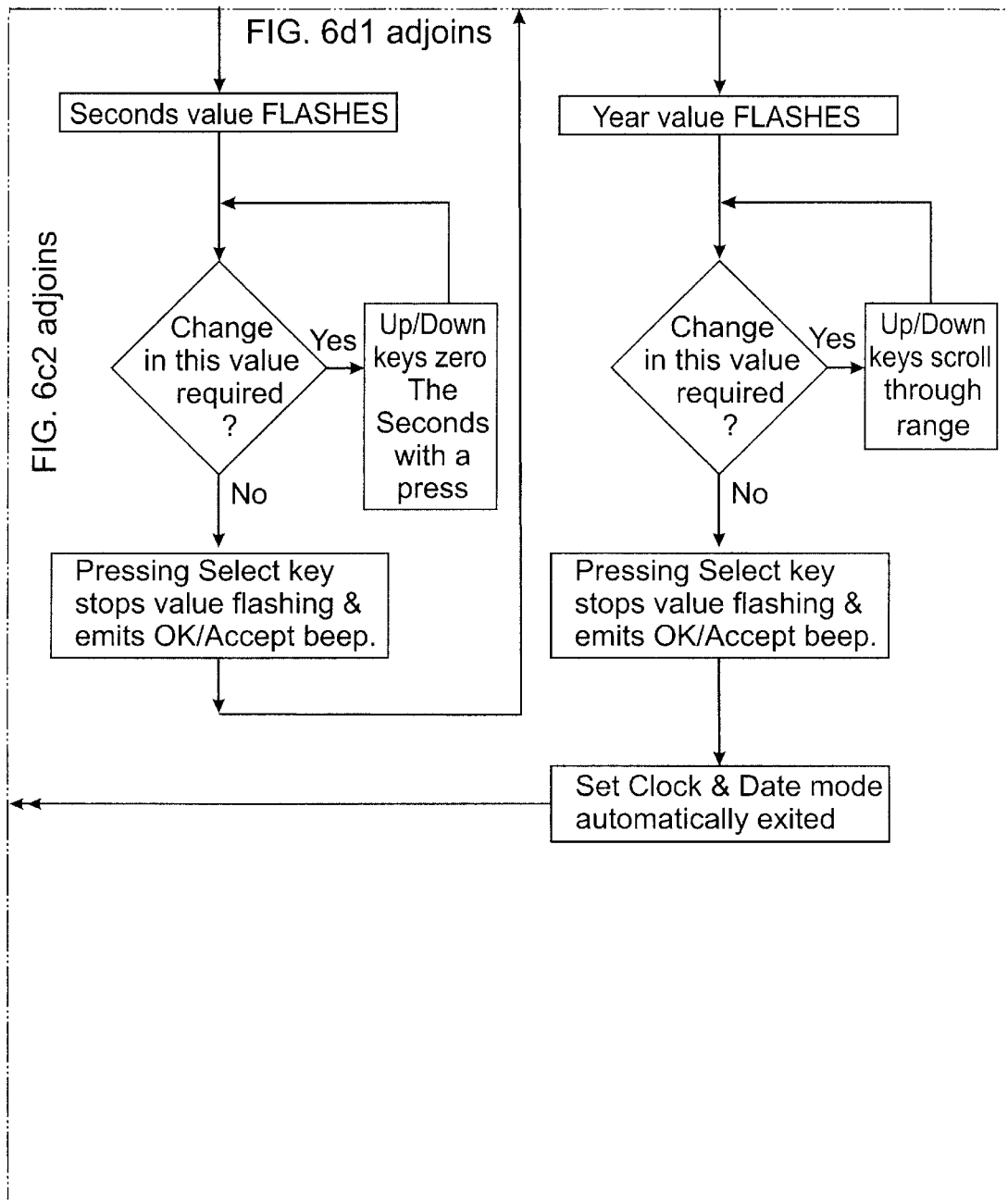
FIG. 6d2

SPINAL MONITOR APPARATUS AND METHOD

This invention relates to a spinal monitor apparatus and method. This invention has particular application to a spinal monitor apparatus and method for use in diagnosis and treatment of lumbar dysfunction and training desirable postural habit and hereinafter this invention will be described in terms of this application. However, it is envisaged that a spinal monitor apparatus and method in accordance with the present invention will find other applications such as on other portions of the spine, or in other applications such as encouraging good lifting practices.

The prevention and treatment of back problems including those caused by poor posture and poor work practices such as unsafe lifting practices is important economically and in terms of quality of life. The underlying causes of poor posture for example are many, and include acquired habits and injury. Treatment may include surgical intervention or physiotherapy, and the use of prostheses such as back braces or corsets. The palliative apparatus are also restrictive, uncomfortable and carry negative social implications. Further, restriction by these means may interfere with nutrition of the intervertebral discs which is usually enhanced or encouraged by flexion in the normal range.

A further problem resides in the fact that the intervertebral discs have a negligible nerve supply. Therefore, under normal circumstances, they feel no pain. When a person habitually assumes incorrect posture (whether sitting, standing or lifting) damage is being done unwittingly because there is no pain to act as a warning of impending and cumulative damage.

The disadvantages of the traditional palliative measures, the limitations of physiotherapeutic treatment and the drastic nature of surgical intervention, have led to development of several non-invasive posture training aids. One of the characteristics of the human spine which distinguishes it from the spine of most other vertebrates is the sinuous form, presenting a substantially concave lumbar region, transforming into a substantially convex dorsal presentation in the thoracic region. A key element in maintenance of good posture and ameliorating or preventing injury is the maintenance of the appropriate lumbar curvature or lordosis. Several prior art apparatus-have been suggested for this purpose.

United Kingdom Patent No. GB-2205039 (Williams) discloses an apparatus for monitoring spinal flexion and including a casing adapted to be supported in the region of the 12th thoracic (or dorsal) vertebra and forming a first reference point and an elongate monitoring member in the form of a resilient extension extending from the casing to bear on the spine in the region of the first sacral vertebra, thus forming a second reference point. In use, the apparatus emits a noise or vibration when the spatial relationship between the second reference point, resiliently biased toward the spine, and the casing, approaches that which would be induced when the reference points correspond to a selected loss of lumbar lordosis.

A disadvantage of the apparatus disclosed in the Williams reference is that the two reference points utilized do not measure the loss of lordosis as such. The apparatus merely monitors the spatial relationship between the two reference points. The disclosed apparatus does not monitor and respond to changes in curvature of the spine directly or indirectly. Where the Williams apparatus does indicate loss of lumbar lordosis, it does so incidentally. With reference to the example disclosed at page 3, line 5 through to 7 of the Williams reference, there is reference to touching the knees and bending over, clearly flexion type movement not directly dependent upon a change occurring in the curvature of a particular portion of the spine.

The Williams apparatus would not detect flattening of the lumbar curve if the user is sitting upright in a chair but still slumping in the lumbar spinal region.

The lumbar curvature may be lost without inclining. This may be demonstrated by the observation that a person may bend forward at the hip joint without flattening the lumbar curvature.

In one aspect the present invention resides broadly in a method for the prevention and treatment of posture deficiencies including the steps of:

monitoring a selected portion of a spine for functions of curvature;

producing a signal corresponding to said monitored curvature, and using said signal to provide an indication of said curvature.

The function of curvature may be selected from the displacement of curvature, rate of change or velocity of curvature, or acceleration of curvature change.

The monitoring of the function of curvature may be continuous or intermittent monitoring. The type of signal generated by the signal means may take any form determined by the choice of monitoring means and signal means, as well as the type of indication of curvature required. The functions of curvature expressed by the indicator means may for example represent displacement of curvature, or alternatively some other function such as rate of change of curvature or accelerations of that rate.

In a further aspect this invention resides broadly in apparatus for the prevention and treatment of posture deficiencies including:

monitoring means adapted to directly or indirectly monitor the curvature of a portion of a spine; and signal means responsive to said monitoring means and adapted to generate a signal indicative of said curvature.

The portion of the spine may be any portion for which conditions of adverse curvature are relevant to matters of prevention, treatment, training or maintainence of posture. Examples include the lumbar, thoracic and cervical spine. The curvature may be in the dorsal, sagittal or any other plane.

The monitoring means may be adapted to monitor the curvature of the selected portion of the spine as a continuous smooth curve or alternatively may monitor the curvature by reference to discrete positions on the spine.

However, where the monitoring of discrete positions on the spine is used, the monitoring means must monitor the actual curvature of the spine directly or indirectly, rather than from inference. Accordingly, where the monitoring means monitors the spatial relationship between discrete selected locations on the spine, there must be at least three of the selected locations to provide a first approximation of the curvature.

The monitoring means may be adapted to monitor curvature and provide a signal dependent on the angular displacement between adjacent monitor elements of a plurality of monitor elements attached to or in contact with the selected plurality of selected spinal locations. Alternatively, the monitoring means may include a unitary body member secured to the selected spinal region and including internal signal generating means responsive to the direct correspondence between the body member and the spinal curve to which it is attached.

The monitoring means may advantageously include a flexible body member adapted to conform in use to the lumbar portion of the wearer's spine, and securing means. The securing means may also take any form consistent with the function of maintaining the body member in position on the wearer. For example, the securing means may comprise one or more of adhesive pads or tape members, straps or any other suitable means. The monitoring means may for example comprise an elastomeric housing having a surface adapted to engage the skin of the user by way of an adhesive layer. For example, the adhesive may comprise a medical grade hypoallergenic adhesive. Preferably the securing means, and indeed the body member and securing means in assembly, are such that they are unobtrusive to avoid embarrassment of the wearer in use. In certain embodiments of the present invention, the securing means may adjustably mount the body member to provide an element of fine-tuning to the positioning the body member relative to the part to be monitored.

The signal means may comprise electromagnetic, electronic, optical, electromechanical, pneumatic or mechanical signal means. Preferably, the monitoring means and signal means are configured such that the mechanical reaction of the apparatus to movement of the spine of the user is minimized such that the user's awareness of the action of the apparatus is minimized. Accordingly, in the case of discrete monitoring elements, the interrelation between the adjacent elements is preferably monitored by optical or electronic means and the signal generated is optical, electronic via an optical coupler, or electronic as appropriate.

The signal means may only provide a signal in response to the, for example, curvature of the spine when it exceeds certain predetermined limits. Accordingly, the signal means may be selected from a wide array of signal means including pressure, temperature, conductivity or proximity signal means. However, it is preferred that the monitoring means provide a continuous output across a range of positions of the monitoring means.

The signal means may include magnetic signal means such as reed switches or inductance devices and accordingly the signal means may include a body mounted portion acting in conjunction with, for example, a magnetic component attached to the wearer. Alternatively, the signal means may comprise an elongate flexible strip of metal or plastic embedded in the flexible body member and having one end adapted to interact with a transducer selected to output a signal corresponding to the curvature. In order that the signal means faithfully reflects the curvature of the monitoring means and thus the spine of the user, there may be provided signal means comprising a metal strip embedded in the elastomeric body of the monitoring means and cantilevered from a relatively rigid portion thereof. A pair of strain gauge transducers may be provided on the opposed flat surfaces of the strip, which may be said to have a ventral surface and a dorsal surface. Thus a differential signal may be generated which corresponds to the curvature of the strip and hence the curvature of the user's spine.

The signal generated by the signal means may interface with indicator means which may include any one or more of vibratory stimuli, audio stimuli, electrical stimuli or a visual indication such as screen based outputs or indication lights. For example, the indicating means may comprise an aversive indication of an adverse static or dynamic curvature and be of an unpleasant or irritating nature to reinforce the maintenance of good posture and to this end it is preferred to utilize a method which involves vibro-tactile stimulus of sub-audible frequency. Alternatively, the indicator means may serve to signal the wearer of the condition such that positive reinforcement of, for example, poor posture habits may be attained. Where the user is receiving a condition responsive indication of adverse posture, this stimulus may be applied immediately or after a selected delay.

Of course, the apparatus may be so configured that both condition responsive and timed stimuli are supplied to the wearer, to indicate poor posture and to stimulate the wearer periodically for voluntary postural variety respectively. The timed stimuli of such apparatus may be user programmable to act as an unobtrusive alarm or reminder system. The timed stimulus may take the form of a mild electric shock, thermal indication, visual indication or soft, audible indication, or any other suitable indication. However, it is preferred that the indicator means again include means capable of generating a vibration to which the wearer's tactile sense can respond, the vibration preferably being of sub-audible frequency and/or volume such that the vibration cannot be detected by others.

The indicator means may be deactivatable to permit gathering of baseline data on the curvature function of the patient.

The signal means may output to indicator means that may be selected from means of recording condition status on a continuous, intermittent or condition responsive basis. For example, for diagnosis and treatment by a health care professional, there may be associated with the apparatus a data terminal or console unit. The console unit may be adapted to receive data comprising a processed version of the signal from the apparatus in real time or batch mode. Alternatively the console may deal with raw signal. The data or signal may be transmitted to the console by cable and/or wirelessly. In a wireless example, a coil may be embedded in the apparatus and adapted to receive and transmit the modulated signal from the signal means via appropriate circuitry.

A power supply may be provided to power the circuitry associated with the preferred apparatus. The power supply may be integral with the body member or securing means, or may be located apart therefrom and connected by suitable wires or the like, such that the power supply may be carried in a pocket. The power supply preferably takes the form of a wireless power supply. For example the power supply may comprise an inductive coil within the monitoring means body and adapted charge rechargeable batteries therein. The inductive charging may be facilitated by a cradle mount for the monitoring means body having an electric field generator in close proximity to the inductive coil when the monitoring means body is so mounted. The inductive coil may perform the alternating duties of radiating member for wireless data transfer and inductive charging coil for maintenance of the batteries.

When used in a rehabilitatory role or posture training role, the console and/or monitor apparatus may advantageously be provided data collection such as with a counter, time base record or the like adapted to record the number and timing of stimuli applied to the wearer by the reacting means. The console may form part of or be connectable to a PC for data processing and statistical analysis to assist in diagnosis and therapeutic design.

The purpose of the preferred embodiments of the present apparatus and method is to provide a method of monitoring in real time, and presenting feedback to the user, data relating to their posture, as measured by the curvature profile of their lower spine relative to an ideal or reference posture. This may be undertaken in the static situation, typically with the user in a sitting position, or in the dynamic situation, with the user undertaking activities ranging from normal day-to-day tasks through to heavy lifting or exercise conditions.

In operation, the preferred apparatus performs a number of specific functions of benefit to the user, including:

(a) postural training, wherein warning the user that their posture has deviated from the ideal reference by a pre-set degree over a pre-set period of time, makes the user aware of the need for postural correction to avoid long-term spinal damage, or the aggravation of a pre-existing condition. Postural training also conditions the postural support muscles and the brain's motor control of these muscles;

(b) postural monitoring, wherein recording over a period of time the user's posture relative to the ideal reference posture and making the recorded data available for analysis by trained personnel, the system allows user behavior which may threaten the health of the spine to be detected and corrected. Faulty equipment such as seating or workstations the use of which may threaten the health of the spine may also be detected and replaced of reconfigured; and/or (c) preventative training, wherein the knowledge that spinal conditions can result from and be aggravated by persistent periods of postural monotony is used in monitoring activity and warning the user of periods of postural monotony which exceed a predetermined elapsed time, such that a certain minimum level of postural variety can be achieved, thereby minimising the risk of this phenomenon.

To achieve these ends the apparatus may be operated in various modes. For example, there may be defined a sitting mode and a lifting mode: These may be pre-set combinations of parameters. The sensitivity of the apparatus and the regimes applies may be variable. For example there may be 3 levels of sensitivity in the sitting mode and in the lifting mode. The user may be able to adjust the underlying values behind the sensitivities (i.e. the levels) but when the product is shipped, the level 1 may be the 'easiest' level (i.e. sensitivity), level 2 may be intermediate and level 3 may be advanced. In other words, level 1 may allow the greatest range of movement before the limits are transgressed, and level 3 may be the smallest (and therefore most difficult) range.

The apparatus may be provided with varying access levels such as normal user access, researcher access, and developer access. Normal user access may be the product's normal access level. Researcher access may allow the user to change the underlying values behind the preset levels whilst absolute values are not revealed—only relative values from the neutral (central) posture. Developer access also allows the underlying values to be changed, but absolute values are displayed, not relative values.

The range of allowable movement within any Level (sensitivity) is not necessarily symmetrical in each direction in the sagittal plane. For example, when the user begins a posture training Session (whereby they receive feedback when their posture goes outside of the desired range), they assume the ideal 'neutral' spinal posture and then press the train key on the console (or it could be on the sensor itself). Pressing the train key enters/logs the neutral posture, around which the allowable range will be calculated. The amount of movement allowed in the flexion (forward-bending) direction is usually more than is allowed in the extension (lumbar-arching) direction. The point is that the range of allowable flexion and extension is not necessarily symmetrical either side of the neutral spinal position. Also, these flexion and extension limits can be adjusted either semi-automatically by choosing a different sensitivity level or manually via the researcher access function.

Preferably, the apparatus and method is not used to provide stringent posture training for many hours on end. A most stringent form of training provided by the apparatus is preferably set in the apparatus, where the user must stay within the desired posture range if a posture transgression is to be avoided. Such a posture training session may begin by (a) the wearer assuming the ideal neutral posture (be that in sitting or standing), and then (b) pressing the train key. Pressing the train key may for example do three things: (1) log the neutral posture for that posture training session, (2) log the date and start time of the posture training session, and (3) begin the countdown timer that will automatically end the posture training session after the allotted time. This may be 5 minutes, 15 minutes, 60 minutes or any period desired—i.e. it is user-defined and variable. This auto-dosage function may help avoid over-training with the apparatus.

The apparatus and method of the present invention lends itself to three distinctly different forms of training: (1) Static posture maintenance, (2) Avoidance of end-range postures, and (3) Avoidance of spinal immobility. Static posture maintenance refers to the posture training sessions whereby the user tries to stay within the prescribed posture range for the duration of the posture training session. During posture training sessions the "out of ideal posture range" feedback is emitted immediately or with only a very small delay (in the order of a few seconds).

Avoidance of end-range postures (e.g. slumping whereby the person's spinal joints 'hang' on their ligaments, thus stretching and damaging them and therefore contributing to the instability and vulnerability of their spine) also involves notifying the wearer when their posture is outside of the desired range, but the feedback is not immediate—it is delayed in the order of minutes; e.g. 1 to 15 minutes. This delayed feedback does not condition the muscles' motor control ability as does more immediate feedback. Instead, the purpose of the delayed feedback is simply to remind the wearer to get out of end-range postures after a number of consecutive minutes of being outside of the ideal posture range. This aims to develop the habit of returning to the neutral range momentarily on a frequent basis throughout the day.

Avoidance of spinal immobility refers to the time-based 'stretch break' reminders. These have a different objective to (2) above. Instead of encouraging the user to briefly return to the neutral range, the stretch break reminders encourage the user to gently move through their full range of motion in all planes-sagittal, lateral and torsional.

The invention will hereinafter be further described with reference to a preferred embodiment thereof as illustrated in the accompanying Figures, wherein:

FIG. 5 is a diagrammatic view of system configurations of the apparatus and methods of FIGS. 1 to 4;

FIGS. 6 to 9 are a flow chart of software functions of apparatus in accordance with the present invention;

Figure 1:
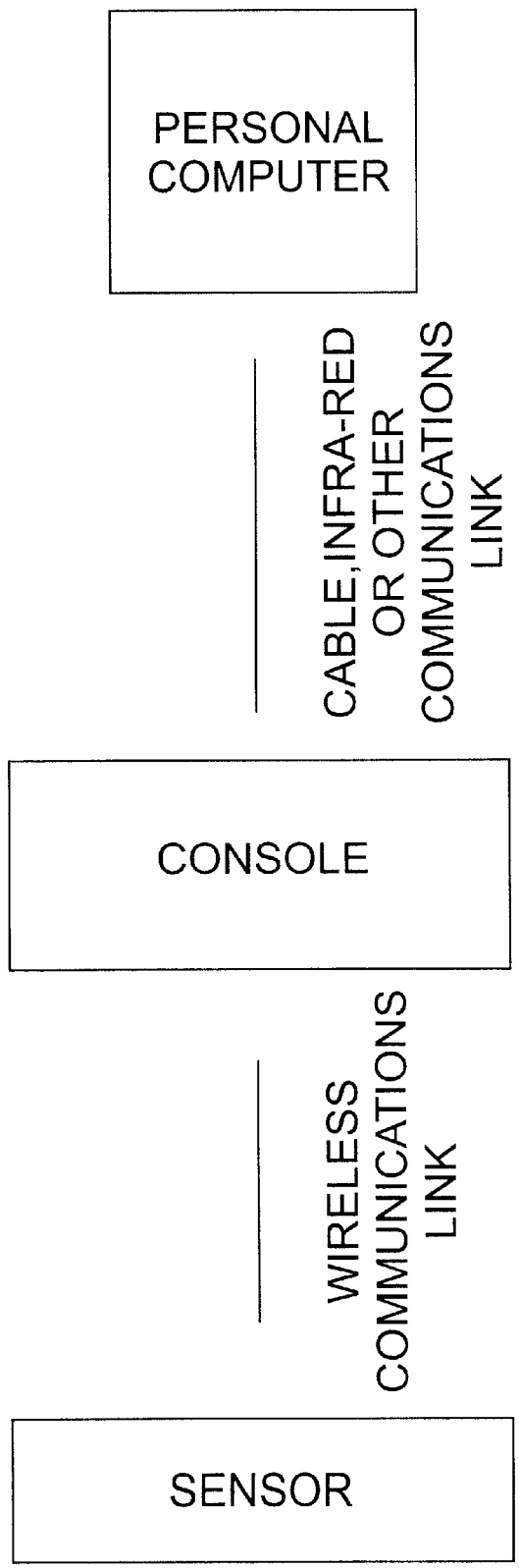
FIG. 1 is a diagrammatic view of an apparatus and method of the present invention.

The present embodiment consists of three main elements, plus a number of ancillary items. With reference to FIG. 1, the main elements include a monitoring apparatus which is attached to the user's lower spine using medical adhesive tape, and performs the function of periodically monitoring spinal curvature by measuring the front-to-back displacement of the vertebra relative to a reference point formed at the junction of the L4 and L5 vertebrae. Displacement is measured by using an elastic cantilever to translate front-to-back movement to a force proportional to the displacement, the force being measured by a force sensor. The configuration enables measurement of both forward movement (arching-or extension) and backwards movement (slumping or flexion) of the lumbar spine. The spinal curvature estimate is processed by the monitoring apparatus to allow warnings to be given to the user; stored in the monitoring apparatus for later retrieval, and conveyed via a wireless communications link to the console for further processing, presentation to the user and storage for later analysis. The monitoring apparatus is powered by a battery which may be recharged from a main derived source, via a contactless power transfer mechanism with the console.

A console may be used either free standing in the vicinity of the user, or may be placed in a pocket, handbag or attached to the user's belt. The console communicates with the monitoring apparatus via a wireless communications link to establish the monitoring apparatus configuration and operating parameters, and to retrieve spinal curvature estimates from the monitoring apparatus for display to the user via a liquid crystal display (LCD). The user may control the console and thence the pad via the console keypad. The console additionally provides facilities for the upload of stored data to a personal computer (PC) which hosts analysis software for the analysis and presentation of recorded data A battery that may be recharged from a mains derived source, via a contact connection, powers the console.

Analysis software consists of a suite of custom software operating on a standard PC, used to retrieve data from the console via a cable based or infra-red connection, and the storage, analysis and presentation to the user of that data. This facility assists in the diagnosis of user behavior which is contributing to spinal damage, and may also be used to trace aberrant behavior, for example, leading to a workplace injury.

Other features include cradles for housing various combinations of monitoring apparatus and console, depending on system configuration, for recharging the batteries in these the monitoring apparatus is described in the following section, with reference to the block diagram of FIG. 2.

In use, the monitoring apparatus is firmly attached to the user's spine using medical adhesive tape. Normally, the reference surface formed by the lower edge of the rigid base of the monitoring apparatus body is attached at the junction of the L4 and L5 vertebrae, with the upper section of the monitoring apparatus body which forms the cantilever attached to the vertebrae immediately above the L4 vertebra. The monitoring apparatus may be attached at other locations on the spine, with an appropriate adjustment made to measurement calibration parameters and set points.

By a method described in more detail hereinafter, the sensing pad produces a voltage output that is related to the curvature of the user's spine by a non-linear but repeatable characteristic. This voltage is periodically sampled and converted to a digital value by an analogue to digital converter that forms a part of the microcontroller. A lookup table stored in the non-volatile memory is used to convert the digital representation of the sampled value to a linearised value that is proportional to spinal curvature, with a fixed constant of proportionality. The lookup table also performs the function of correcting unit to unit variations in sensing pad characteristics that result from differences during manufacture, so that the spinal curvature estimate is consistent between monitoring apparatus units. This correction is achieved as a part of a calibration process undertaken during monitoring apparatus manufacture. Spinal curvature sample estimates are measured at frequent intervals, typically up to 4 times per second, or at a lower rate depending on the operating mode. Depending on the monitoring apparatus operating mode, the data may be processed in a number of ways.

In an operating mode where the monitoring apparatus is operated in a stand-alone mode, hereinafter referred to as "sensor autonomous mode", spinal curvature estimates may be processed by the microcontroller, using an algorithm which determines whether the user should be warned of bad posture. Using operating parameters and set points downloaded to the monitoring apparatus from the console during the monitoring apparatus setup procedure, the algorithm determines when the conditions for a warning to be delivered to the user have been satisfied, and alerts the user via a vibration generated under microcontroller control via the vibrating motor. The monitoring apparatus is thus operating autonomously during the period where the user is wearing the monitoring apparatus in this mode. The algorithm takes into account the degree of spinal curvature from a reference position established during set-up, the number of transgressions which have occurred during a time period, and the number of warnings given to the user over a period of time, and the duration of the transgression. A number of settings of these parameters are provided for, to allow for the skill and experience of the user in using the system, and the severity of the condition being monitored. That is, the strictness of the training can be varied.

When the optional high capacity non-volatile memory and optional real-time clock (RTC) are fitted, spinal curvature sample data is time stamped with time information read from the real-time clock, and stored in the monitoring apparatus non-volatile memory, for later retrieval by the console and subsequent uploading to the PC for processing.

When the monitoring apparatus is operating in conjunction with a console, spinal curvature estimates are periodically uploaded to the console, typically at a rate lower than the sampling rate, with the option of a number of samples being preprocessed by the monitoring apparatus prior to uploading (e.g. by averaging several samples). In this configuration, the algorithm that determines when the conditions for a warning to be delivered to the user have been satisfied, is implemented by the console which also displays a range of information relating to user activity. When the transgression alert is required, the console conveys the appropriate command to the monitoring apparatus, which in turn alerts the user via a vibration generated under microcontroller control via the vibrating motor. Time-stamped spinal curvature sample data is stored in the console non-volatile memory, for later uploading to the PC for processing This mode of operation is particularly useful during user training, or intensive monitoring of a user by a trained operator.

The monitoring apparatus undertakes bi-directional communications with the console via a wireless bidirectional link, implemented using magnetically coupled communications between a coil located in the monitoring apparatus, and corresponding coil (or optionally, two coils mounted with axes orthogonal) in the console. Amplitude modulation of a low frequency radio frequency carrier at frequencies typically in the vicinity of 50 kHz to 100 kHz is used to convey information between the monitoring apparatus and console. A master/slave poll-response message exchange strategy is used, with the monitoring apparatus normally acting as master (although the console can act as master during monitoring apparatus set-up or other operating modes). Each monitoring apparatus has a unique identity, which is used by the console and monitoring apparatus associated with that console to allow communications between that pair of units, and to ignore signals from other non-associated units which may be operating in the vicinity.

Figure 2:
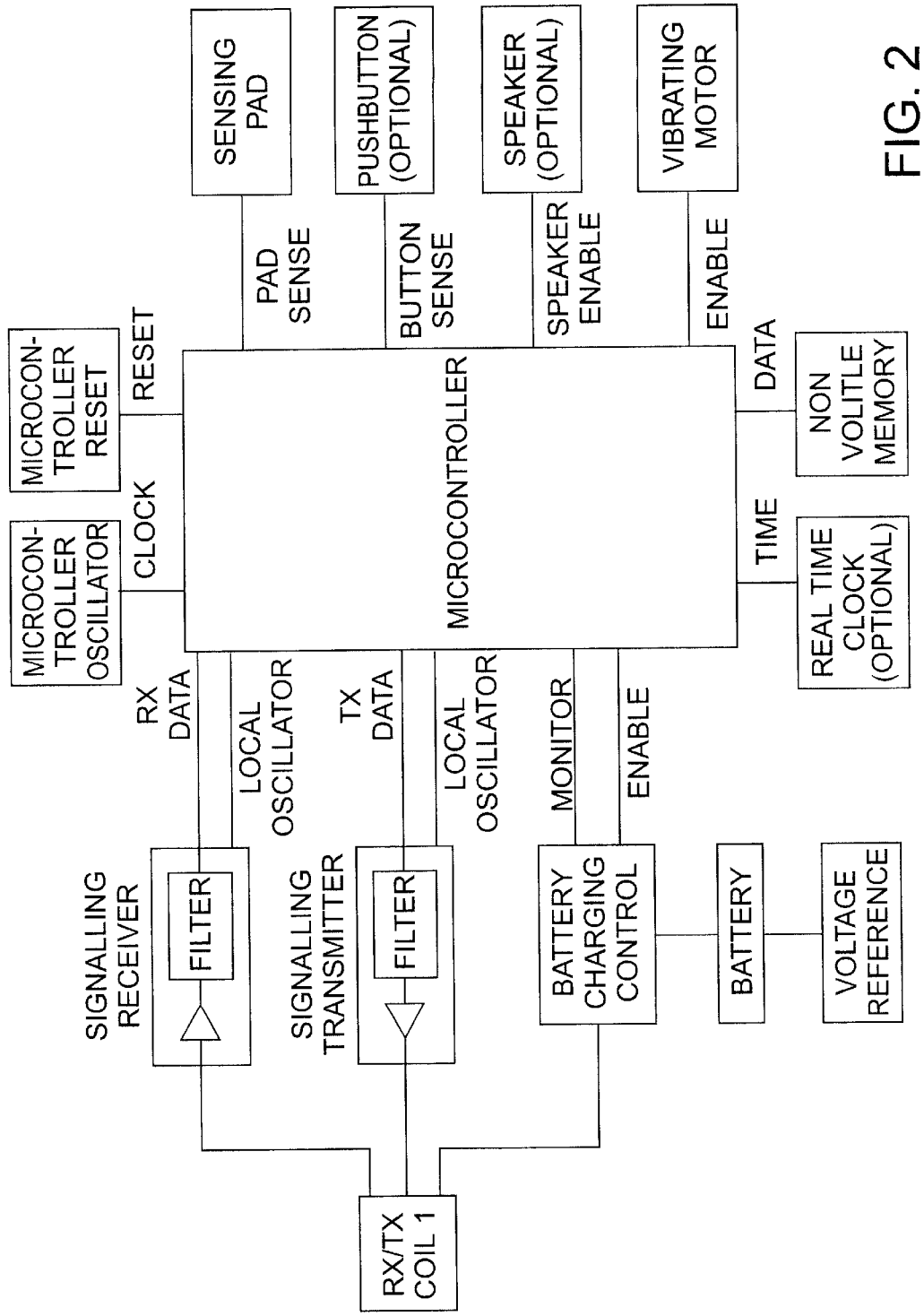
FIG. 2 is a diagrammatic view of a monitoring apparatus suitable for use in the apparatus and method of FIG. 1.

With reference to FIG. 2, a local oscillator signal at the transmission frequency is generated by the microcontroller is connected to the signalling transmitter, and amplitude modulated by on/off switching by the TX modulator in accordance with the logic state on the TX data signal. Messages to be transmitted from the monitoring apparatus to the console over ranges typically up to 1 metre are encoded with framing and checksum protection information, and are encoded to guarantee an adequate density of transitions to allow effective bit timing recovery in the corresponding receiver. After amplification, the transmit signal is applied to the transmit winding of the receive/transmit coil.

Signalling messages received by the monitoring apparatus are coupled from the receive winding of the RX/TX coil to the signalling receiver, whence they are amplified and mixed down to an intermediate frequency (IF) by mixing with an offset local oscillator and then filtered. The Microcontroller then samples the resultant RX data signal which is modulated at the IF using I and Q sampling, via an analogue to digital converter contained with in the microcontroller. A processing algorithm implemented in microcontroller firmware is used to regenerate the transmitted modulating signal, which is further processed to implement bit timing recovery, message framing and checksum checking.

In difficult communications situations, frequency diversity is used to avoid narrowband interference from devices such as computer screens. If communications cannot be established on one of a number of operating frequencies, alternative frequencies will be automatically tried in turn until reliable communications is established.

The monitoring apparatus is powered by a rechargeable battery, which is charged by a magnetically coupled radio frequency signal derived from the console, or a charging adapter used specifically for the purpose. In the battery charging mode, the monitoring apparatus is intimately coupled with the console by locating the monitoring apparatus in a receptacle provided on the console for the purpose. In alternative configurations the coupling is achieved between the console and monitoring apparatus by locating bath in an adapter provided for the purpose; or the monitoring apparatus is placed into the charging adapter which provides the charging signal.

With reference to FIG. 2, in the battery charging configuration the charging signal is coupled from the battery charging winding on the receive/transmit coil, to the battery charging control, which is enabled by the microcontroller when battery charging is required. When charging is enabled, received charging energy is rectified and applied to the battery. If charging is not required or has been completed, the microcontroller will disable battery charging, which can be sensed by the console due to the resultant change in impedance seen by its power signal transmitter, allowing the console in turn to deactivate charging. The microcontroller monitors charging via the monitor signal connected to an analogue to digital converter internal to the microcontroller. When the battery is depleted to the extent that insufficient voltage is available to operate the microcontroller, the enable signal is arranged to become active, to ensure that battery charging will occur to subsequently allow the monitoring apparatus to become active.

The battery provides the operating voltage to the microcontroller and other functional blocks, including the voltage reference which generates stable reference voltages required by other monitoring apparatus functional modules.

All functions of the monitoring apparatus are controlled by operating firmware hosted by the microcontroller. The microcontroller is implemented by a single chip 8-bit microcontroller with built in analogue to digital converter channels, and which is available in one-time programmable or mask programmable form. The clock signal required for normal microcontroller operation is provided by the microcontroller oscillator consisting of a ceramic resonator. The microcontroller reset circuit monitors battery voltage, and resets the microcontroller whenever inadequate supply voltage is available. The microcontroller includes an internal watchdog reset circuit which resets program operation in the event of failure of normal operation.

In order to minimise the current drawn from the monitoring apparatus battery and hence maximise the time between re-charges, the microcontroller incorporates measures to ensure that the low-current Idle state of operation is adopted for as great an amount of time as possible. When a user monitoring or training session is not in progress, the monitoring apparatus remains idle for the majority of the time, activating only periodically to sense for signalling messages from a console which indicate that the monitoring apparatus should become active to receive instructions from the console.

The monitoring apparatus may be equipped with an optional pushbutton switch and speaker. The pushbutton may be used to activate and deactivate the monitoring apparatus; to place the monitoring apparatus in a condition where it attempts to establish communications with a console for association, setup and data upload functions, and to initiate or terminate training and monitoring sessions. The optional speaker is used in conjunction with the pushbutton to provide feedback to the user when pushbutton functions are being implemented. The monitoring apparatus is configured as a fully sealed unit, without external electrical connections, to minimise problems encountered through contact with body fluids and cleaning fluids.

The function of the monitoring apparatus is to provide an estimate of the curvature of the spine, relative to a reference position established at the commencement of each training or monitoring session The measurement method is explained with reference to FIG. 3 which is drawn in exaggerated scale for clarity. The analysis presented below is simplistic in that the distributed nature of applied forces is not taken into account; rather, moments about the pivot point are considered in terms of the equivalent point force operating at a prescribed distance from the pivot point, equivalent to the integrated moment about the pivot point resulting from the distributed force which the point force represents. Additionally, second order and nonlinear effects are not considered in the analysis.

The sensing pad provides a measurement of spinal displacement in the horizontal plane at vertebrae immediately above vertebra L4, relative to an axis formed by vertebra L4 and L5, and hence provides an estimate of the curvature of the lower spine. Displacement of the spine at the end of the cantilever furthest from the pivot point is denoted as Ds for slump (ie forward bending) and Da for arch (ie backwards bending). Assuming linear mechanical operation, the cantilever of spring constant K will require net forces at the far end of the cantilever of Fs=KDs to cause slump displacement Ds, and Fa=KDa to cause arch displacement Da.

Displacements Ds and Da are sensed by force sensor, coupled to the cantilever by a coupling pad which absorbs any longitudinal movement (ie sliding) and thus prevents wear of the force sensor. The force sensor resistance changes with the total force applied to the sensor active area, this resistance change being converted to a voltage measured by the microcontroller analogue to digital converter, by current flowing through the force sensor.

The nature of the force sensor is that it is able to measure only positive forces applied to it, requiring the coupling pad to maintain continuous contact with the force sensor. This is achieved in practice by applying a pre-load force Fp to the cantilever, to ensure that for maximum arch condition Fa, the force Fm applied to the force sensor remains positive.

Figure 3:
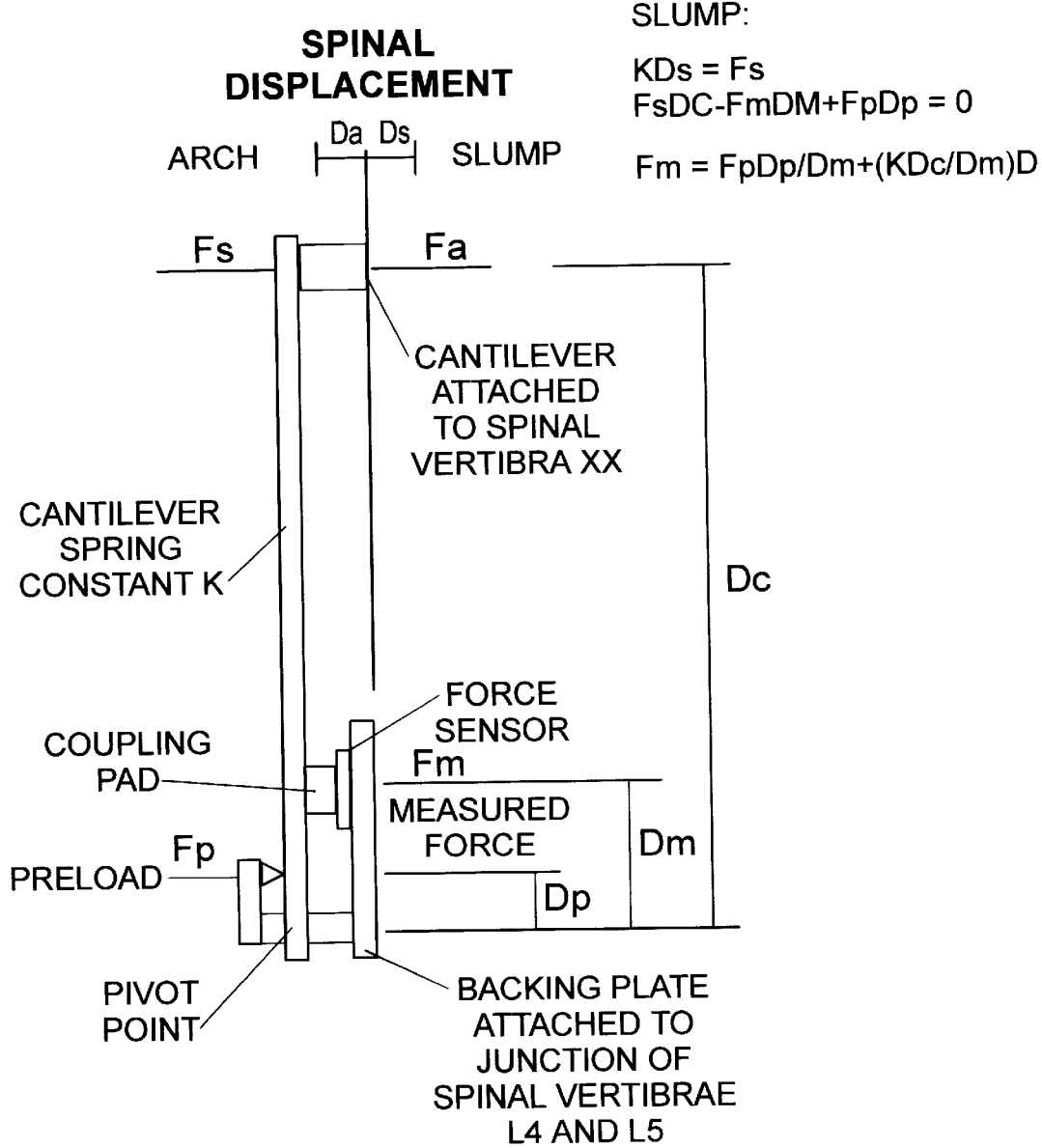
FIG. 3 is a diagrammatic view of the principle of operation of the monitoring apparatus of FIG. 2.

With reference to FIG. 3, the force equations relating measured force Fm to Ds for slump and Da for arch are readily apparent.

Non-linearities and unit to unit variations resulting from the characteristics of the force sensor, the materials used and second order effects can be readily compensated by the use of a calibration procedure during manufacture, with a calibration lookup table being stored in monitoring apparatus non-volatile memory. If necessary, re-calibration during the life of the monitoring apparatus can be achieved by updating the calibration lookup table.

For reliable and repeatable operation, it is important that the monitoring apparatus mechanics and the force sensor be designed to avoid wear, hysteresis effects or changed of characteristics with temperature, humidity, atmospheric pressure and age.

The console is described in the following section, with reference to the block diagram of FIG. 4. In use, the console is located either free standing on a convenient surface, or in a purse, pocket or attached to the user's belt To effect an interface the console must be located within radio range of the monitoring apparatus, typically up to 1 metre. During programming and monitoring operations, the console must be located so that the user may view its display. Additionally, during programming, its keypad is operated by the user. During communications with the PC, the console is located in an interface adapter and thence connected to the PC interface.

When the console is operating in conjunction with a monitoring apparatus, the console communicates with the monitoring apparatus to upload spinal curvature estimates, which are processed, stored, displayed to the user. When required, the console conveys a command to the monitoring apparatus to deliver a warning to the user. This method of operation is described fully in the section above dealing with monitoring apparatus operation.

Spinal curvature data received from the monitoring apparatus is date and time-stamped with time information from the real-time clock, and stored in the console non-volatile memory, for subsequent uploading to the PC for processing.

When the monitoring apparatus is to be used in autonomous mode, the console is used to set up the configuration required for the training or monitoring activity, and download these settings to the monitoring apparatus. On completion of the training or monitoring activity, communications is established between the console and monitoring apparatus, and data gathered during the activity uploaded to the console for processing, display to the user and subsequent uploading to the PC.

The console undertakes bidirectional communications with the monitoring apparatus via a wireless bi-directional link, implemented using magnetically coupled communications between one and optionally a second coil, and the corresponding coil in the monitoring apparatus. Two coils located with axes orthogonal to one another are provided to allow reliable communications to be established with a range of relative angular orientations between the console and monitoring apparatus.

Figure 4:
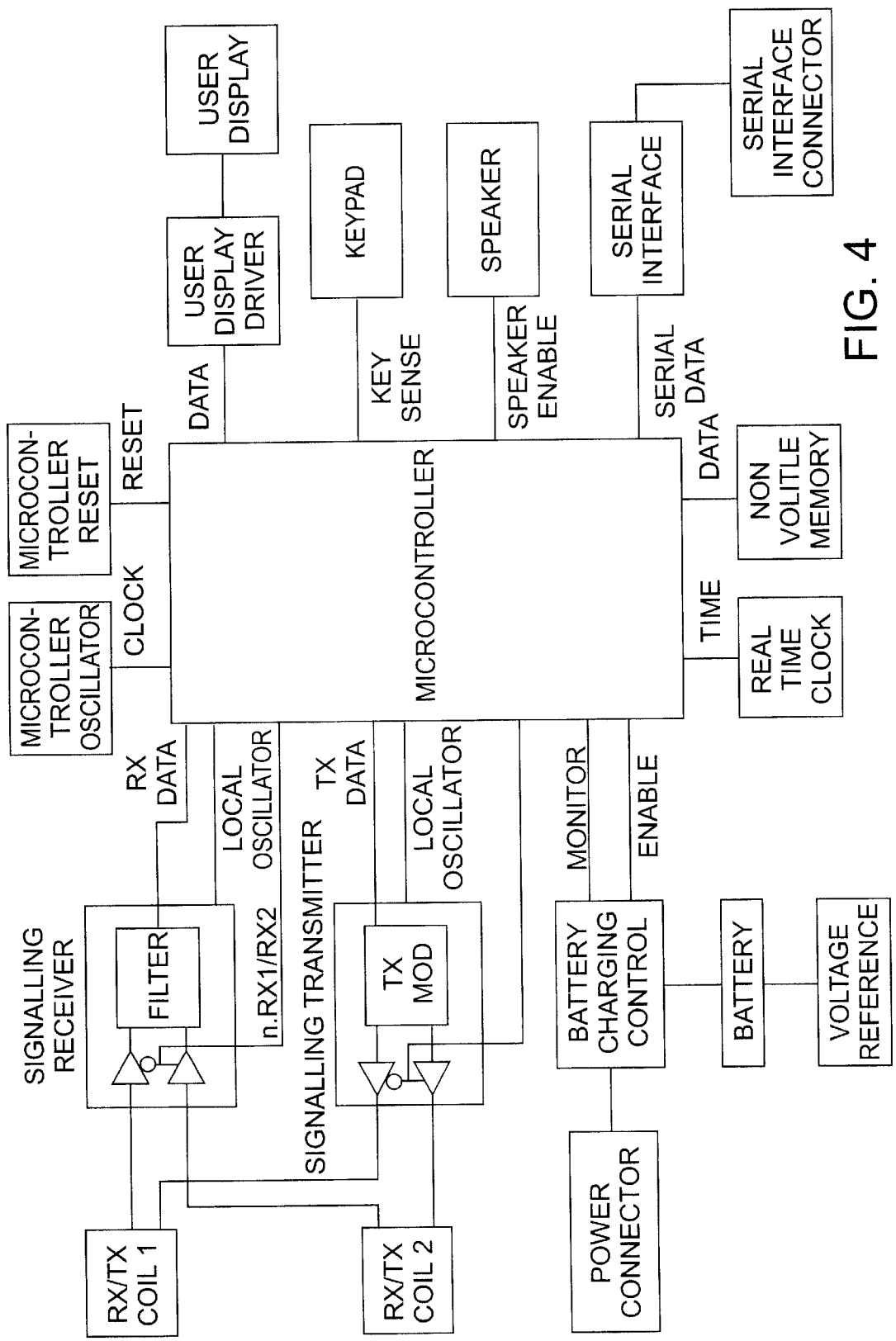
FIG. 4 is a diagrammatic view of a console suitable for use in the apparatus and method of FIG. 1.
Figure 7A:
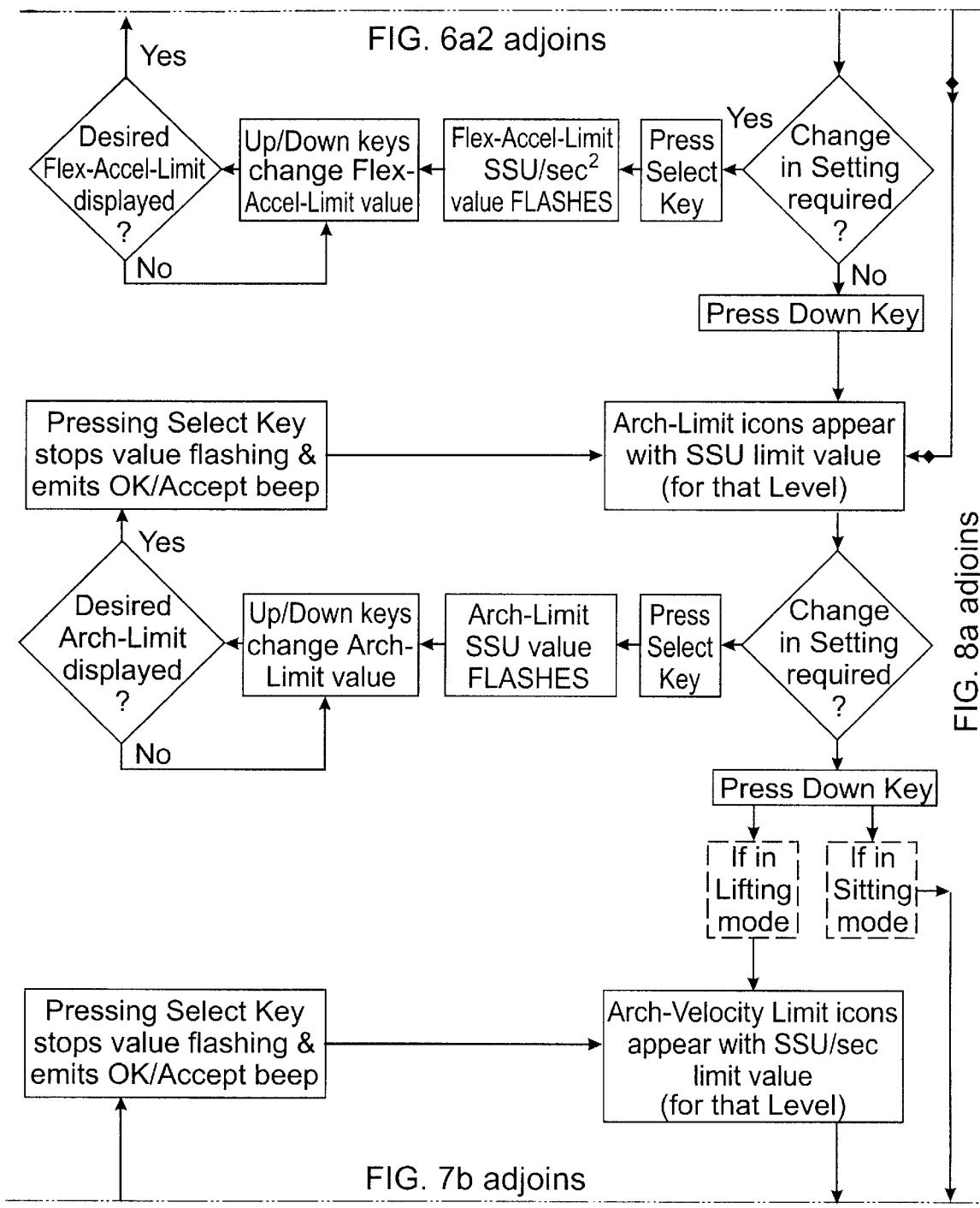
Figure 7B:
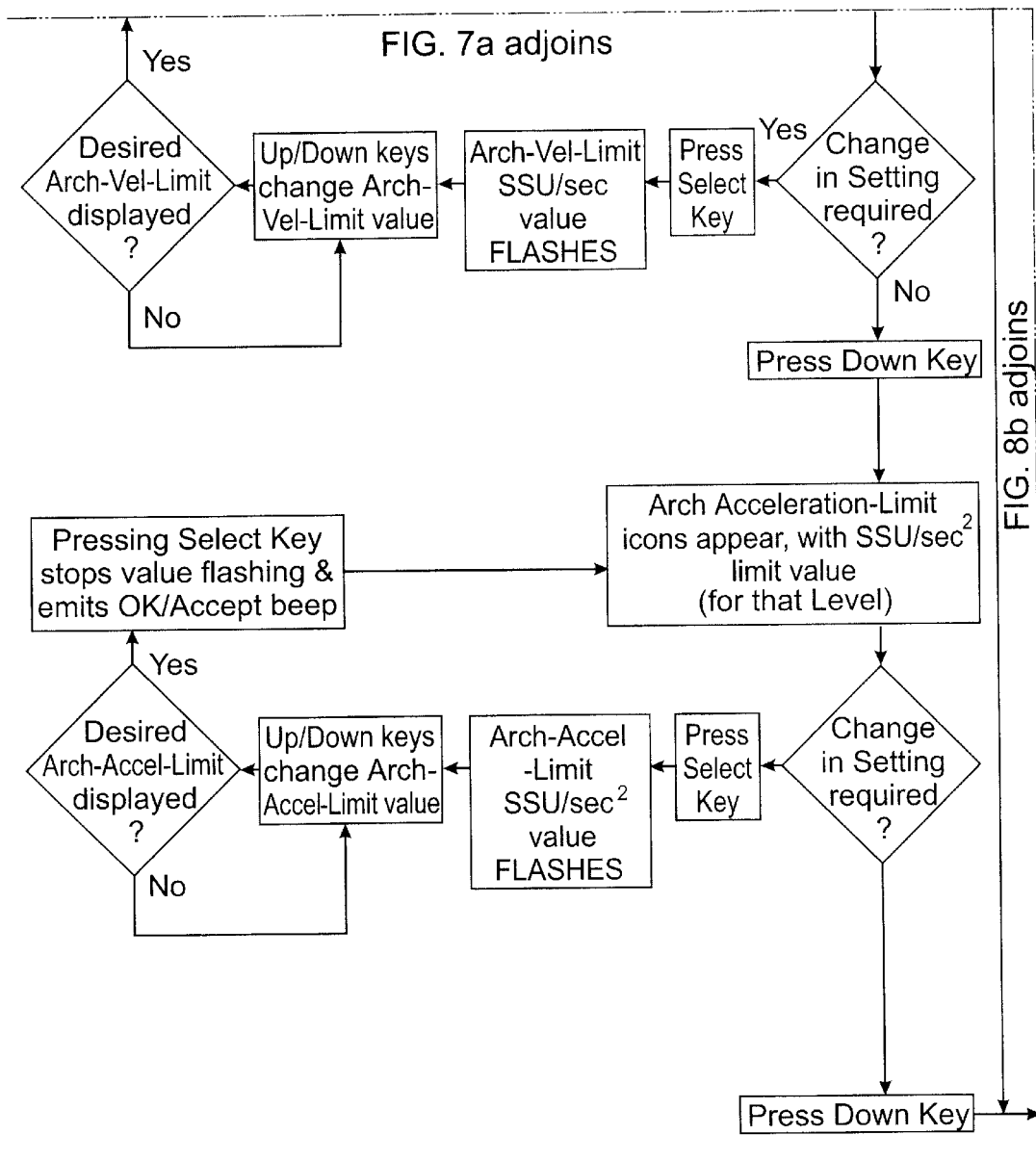
Figure 8A:
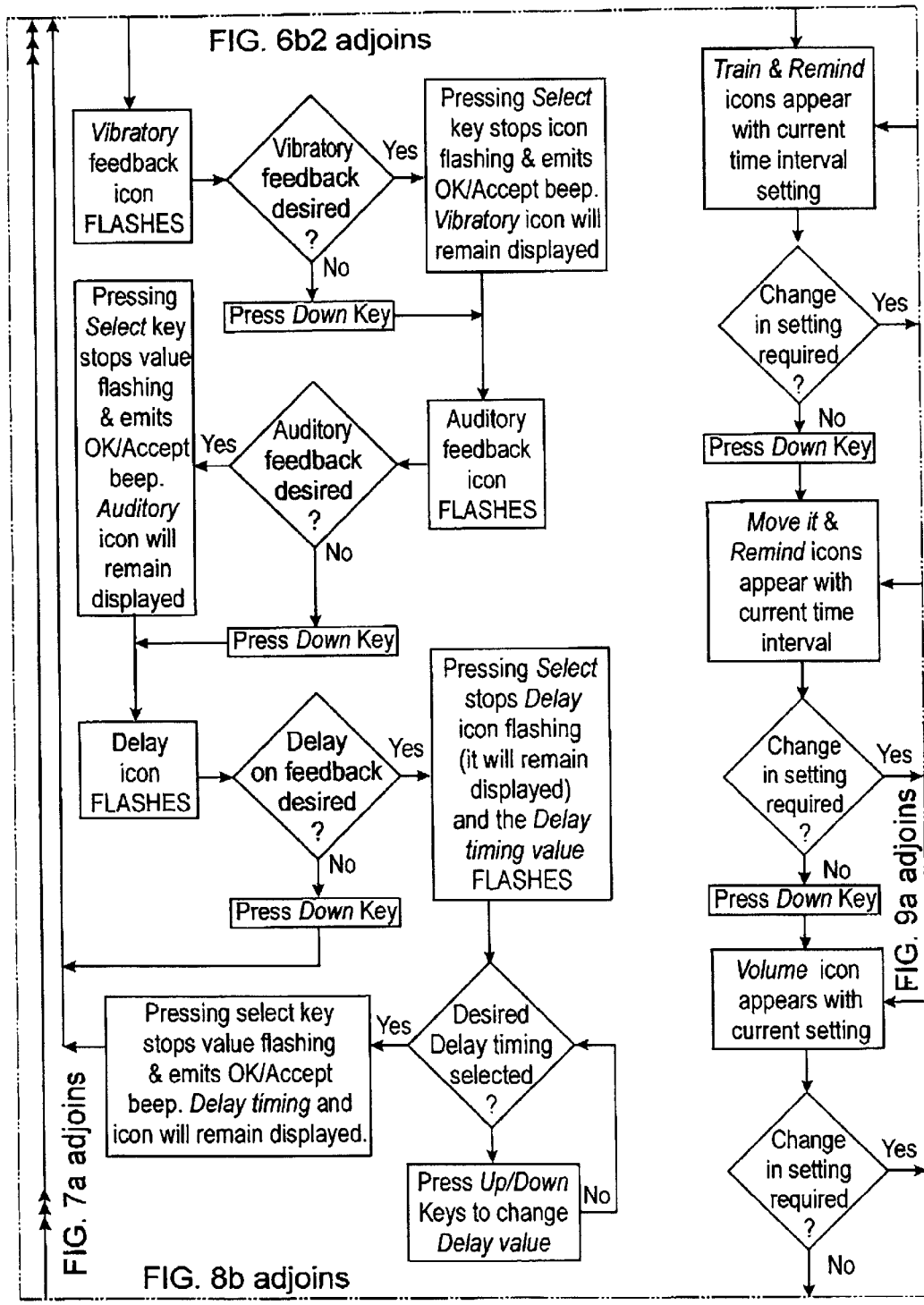
Figure 8B:
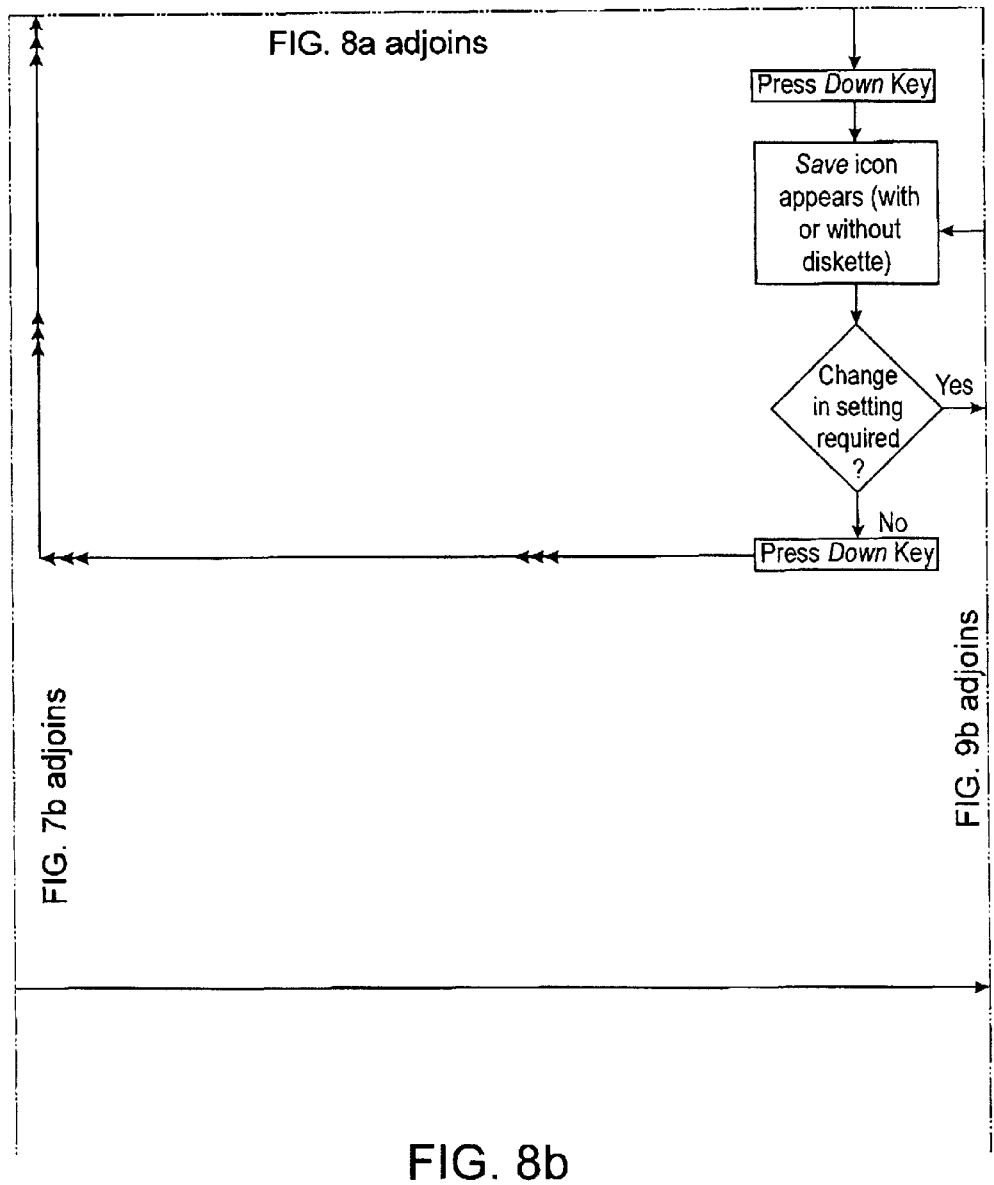
Figure 9A:
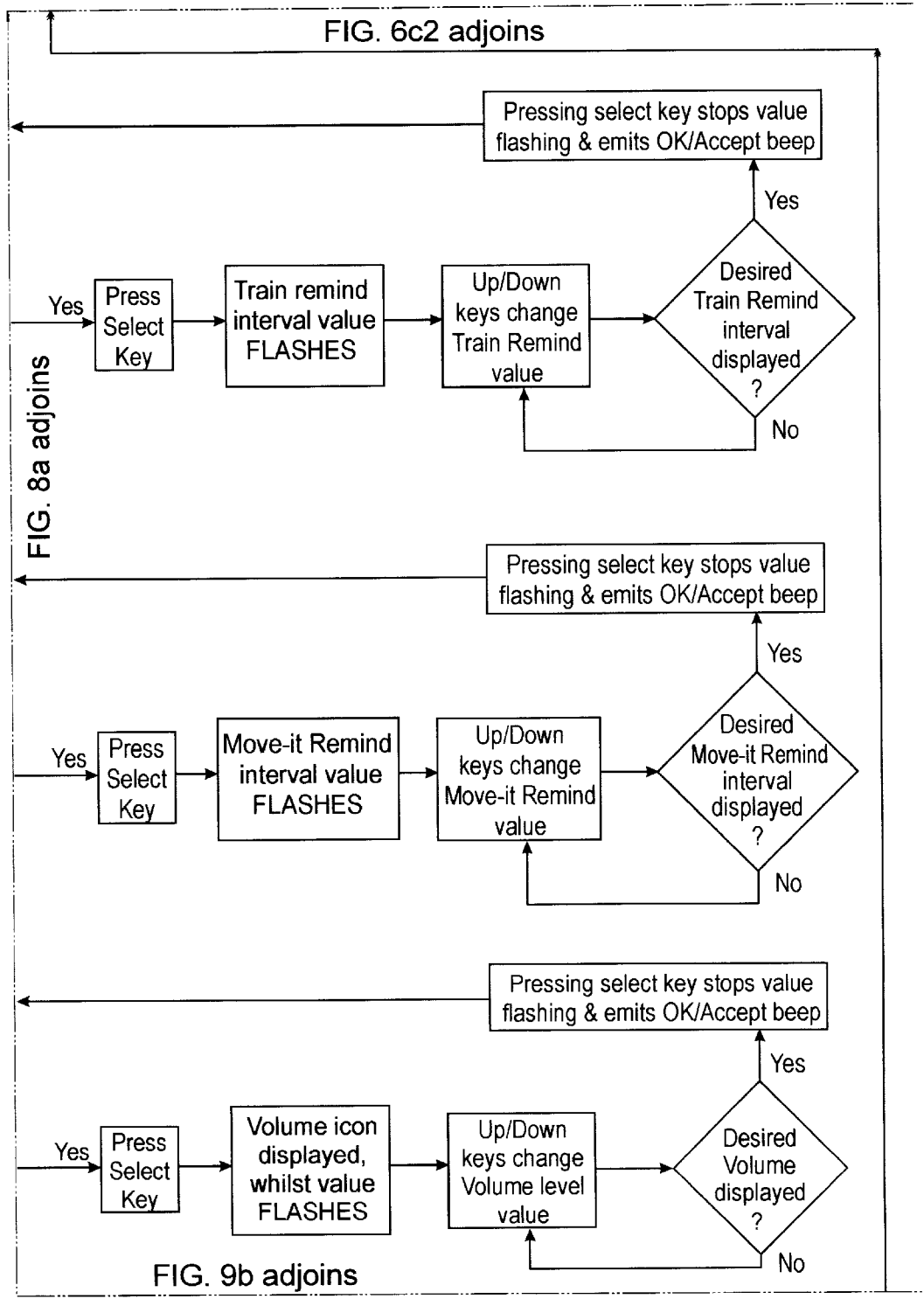
Figure 9B:
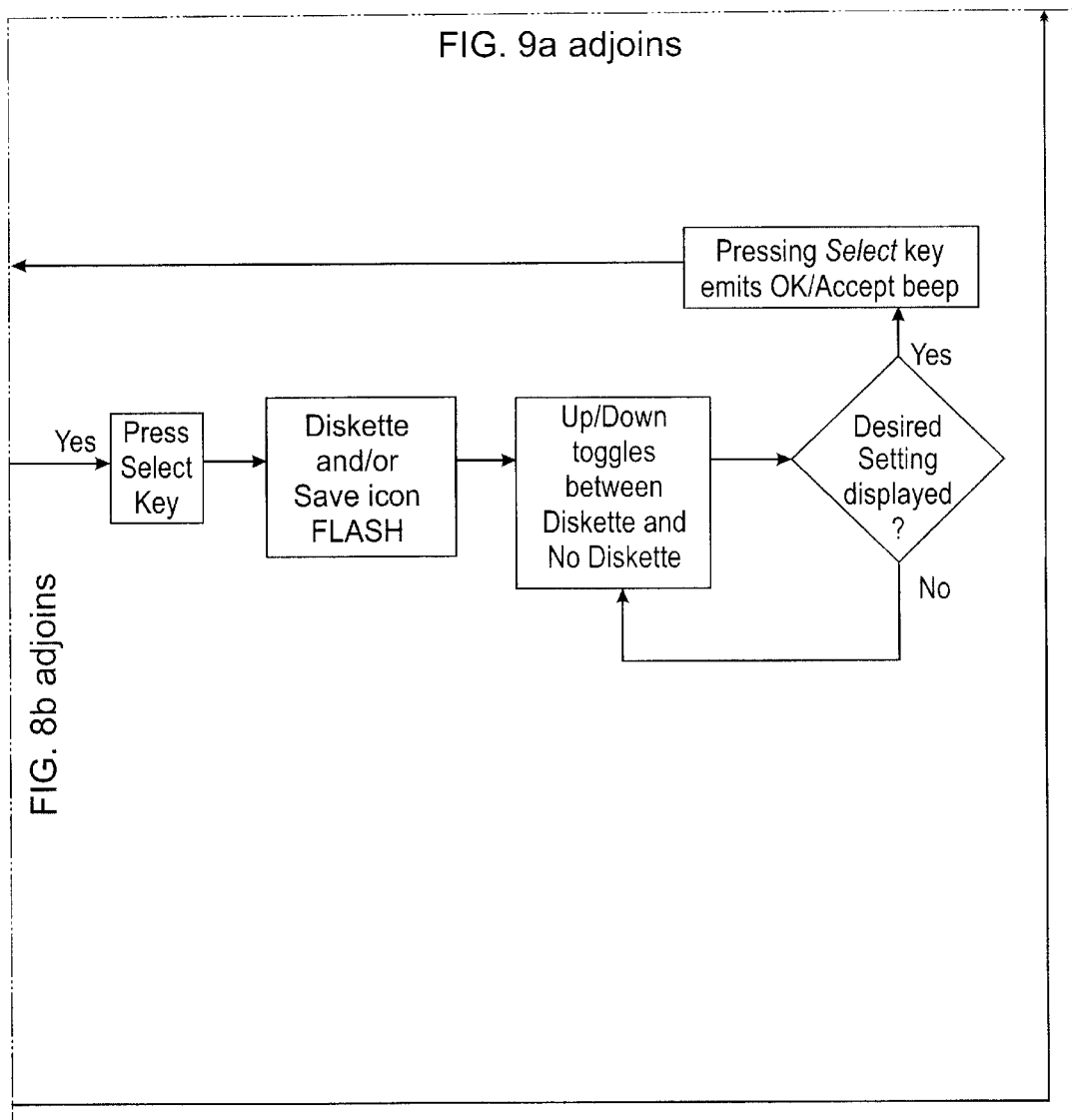

With reference to FIG. 4, a local oscillator signal at the transmission frequency is generated by the microcontroller, connected to the signalling transmitter, and amplitude modulated by on/off switching by the TX modulator in accordance with the logic state on the TX data signal. After amplification by the one of the two amplifiers activated by the n.TX1/TX2 signal, the transmit signal is applied to the transmit winding of either receive/transmit Coil 1 or receive/transmit Coil 2.

Signalling messages received by the console are coupled from the receive winding of RX/TX coil 1 and RX/TX coil 2, to the signalling receiver, whence they are amplified by one of the two amplifiers enabled by the n.RX1/RX2 signal, mixed with an offset local oscillator and then filtered. The microcontroller then samples the resultant RX data signal which is modulated at the IF using I and Q sampling, via an analogue to digital converter contained with in the microcontroller. A processing algorithm implemented in microcontroller firmware is used to regenerate the transmit modulating signal, which is further processed to implement bit timing recovery, message framing and checksum checking.

In difficult communications situations, frequency diversity may be used to avoid narrowband interference from devices such as computer screens. If communications cannot be established on one of a number of operating frequencies, alternative frequencies may be automatically tried in turn until reliable communications is established.

The console may be powered by a rechargeable battery, which is charged by an external mains derived source electrically connected either directly to the console, or in alternative configurations via an interface adapter.

With reference to FIG. 4, in the battery charging configuration the mains derived power source is connected to the battery charging control, which is enabled by the microcontroller when battery charging is required. When charging is enabled, received charging energy is rectified and applied to the battery. If charging is not required or has been completed, the microcontroller will disable battery charging. The microcontroller monitors charging via the monitor signal connected to an analogue to digital converter internal to the microcontroller. When the battery is depleted to the extent that insufficient voltage is available to operate the microcontroller, the enable signal is arranged to become active, to ensure that battery charging will occur to subsequently allow the monitoring apparatus to become active.

The battery provides the operating voltage to the microcontroller and other functional blocks, including the voltage reference which generates stable reference voltages required by other monitoring apparatus functional modules.

Additionally in the battery charging mode, a monitoring apparatus may be intimately coupled with the console by locating the monitoring apparatus in a receptacle provided on the console for the purpose. In alternative configurations the coupling is achieved between the console and monitoring apparatus by locating both in an adapter provided for the purpose, or the monitoring apparatus is placed into the charging adapter which provides the charging signal. Via its signalling transmitter and RX/TX coil 1, the console is able to provide energy to recharge the monitoring apparatus battery. By measuring the impedance presented to RX/TX coil 1, the console is able to determine when monitoring apparatus charging has been disabled by the monitoring apparatus microcontroller, deactivate the charging function and notify the user via the console display.

All functions of the console are controlled by operating firmware hosted by the microcontroller. The microcontroller is implemented by a single chip 8 bit microcontroller with built in analogue to digital converter channels, and which is available in one-time programmable or mask programmable form. The clock signal required for normal microcontroller operation is provided by the microcontroller oscillator consisting of a ceramic resonator. The microcontroller reset circuit monitors battery voltage, and resets the microcontroller whenever inadequate supply voltage is available. The microcontroller includes an internal watchdog reset circuit which resets program operation in the event of failure of normal operation.

In order to minimise the current drawn from the console battery and hence maximise the time between re-charges, the microcontroller incorporates measures to ensure that the low-current Idle state of operation is adopted for as great an amount of time as possible. When a user monitoring or training session is not in progress, the console remains idle until activated by a keystroke by the user. On completion of the session, the console returns to the idle condition.

The console may be equipped with a user display driver and user display for the presentation of information to the user, including data required to configure the monitoring apparatus, and information gathered during training and monitoring sessions.

The console is equipped with a keypad for general control and user interface functions, and speaker to provide feedback to the user when keypad and other functions are being implemented.

The console is equipped with an electrically connected serial interface for connection to a PC for the uploading of time-stamped data gathered during training or monitoring sessions. The connection to the PC is made via an interface adapter, which may provide a direct electrical connection between the console and PC for RS-232 connections, or signal processing for connection by other standard means such as universal serial bus or infra-red connection.

Data exchange between the console and PC is via a message based protocol employing checksum protection and retransmission capability to ensure error free data transfer.

The software on the preferred PC console based system is the subject of the flow chart comprising FIGS. 6 to 9. The objective of the software is to facilitate detailed analysis of the data collected by the apparatus in order to monitor a patient's posture improvement progress and to detect activities of daily living and lifestyle habits that may be increasing the patients' risk of back injury or recurrence of back pain. The software is also used to keep case management records and patient communication functions.

The plug pack provides a rectified and filtered DC supply derived from a standard mains source, to provide power to system elements during battery charging. The console may also be operated from the mains derived power source. The monitoring apparatus charger provides battery charging energy to a monitoring apparatus in a manner similar to the console, when a monitoring apparatus is to be recharged. Operation is similar to the monitoring apparatus battery charging function of the console. The monitoring apparatus charger charging bay locates the monitoring apparatus in the correct orientation for battery charging, but makes no physical electrical contact to the monitoring apparatus, in that inductive coupling or RF charging is used.

The interface adapter and charger provides mains-derived power from the plug pack to the console, via an electrical connection from the adapter to the console. This power source is used to power the console, recharge the console battery and when a monitoring apparatus is coupled to the console, recharge the monitoring apparatus battery via wireless coupling. Electrical connections are also provided to the console for connection to the PC.

The multi-monitoring apparatus interface adapter and charger provides mains-derived power from the plug pack to the console, via an electrical connection form the adapter to the console. This power is used to power the console, recharge the console battery and when a monitoring apparatus is coupled to the console, recharge the monitoring apparatus battery via wireless coupling Additionally, the multi-monitoring apparatus interface adapter and charger provides battery charging energy to additional monitoring apparatus in a manner similar to the console, when a monitoring apparatus used in the multi-monitoring apparatus configuration are to be recharged. Operation is similar to the monitoring apparatus battery charging function of the console. Electrical connections are also provided to the console for connection to the PC.

With reference to FIG. 5, the present system, may be used in a number of system configurations. Each configuration is depicted as set up for battery charging, to allow the incorporated elements to be clearly determined.

The standard console/monitoring apparatus system involves the provision to the user of a single console and monitoring apparatus, along with a plug pack for console and monitoring apparatus battery charging. The monitoring apparatus is typically used in conjunction with the console, although the monitoring apparatus may be used in the stand-alone mode, for example when the monitoring apparatus attached to the user modes out of communications range of the console.

The console/monitoring apparatus PC interface system operates in a similar fashion to the standard configuration, with the addition of the interface adapter and charger which allows the console to be connected to the PC for data upload and analysis. The stand alone monitoring apparatus system in FIG. 18 involves the provision to the user of a single monitoring apparatus, along with a plug pack 173 and monitoring apparatus charger 174 for monitoring apparatus battery charging. The monitoring apparatus is pre-programmed to suit user requirements, typically using a console possessed by a practitioner. The monitoring apparatus is used in the stand-alone mode, and may subsequently be returned to the practitioner for data upload and reprogramming.

The console/multi-monitoring apparatus PC interface system operates in a similar fashion to the console/monitoring apparatus PC interface system, with the provision of charging facilities for additional monitoring apparatus. This configuration is useful in an environment where a number of users are directed by a practitioner in an environment such as a clinic.

Figure 10:
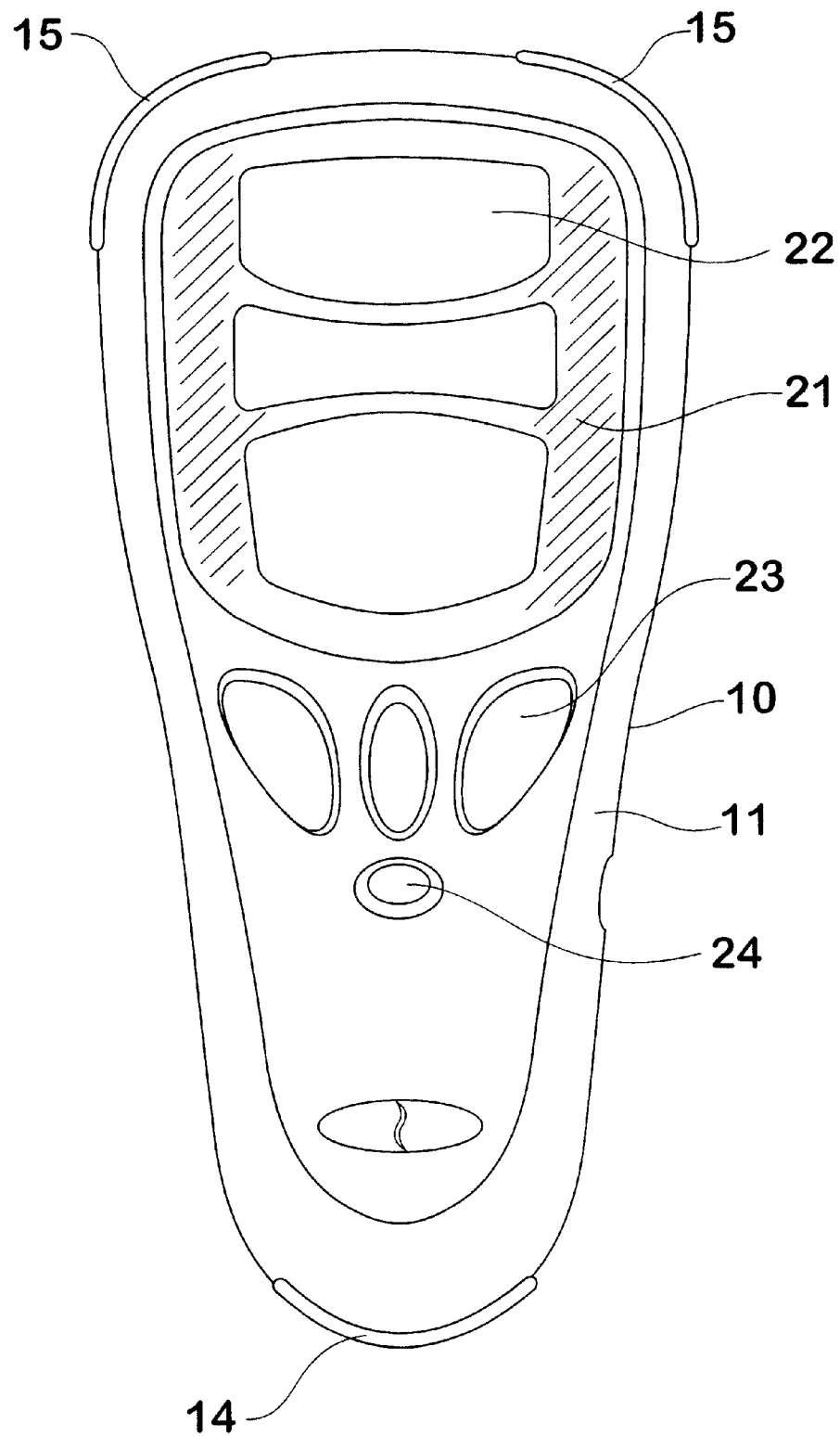
FIG. 10 is an exploded three-quarter perspective view of a monitoring apparatus suitable for use in the present invention.
Figure 11:
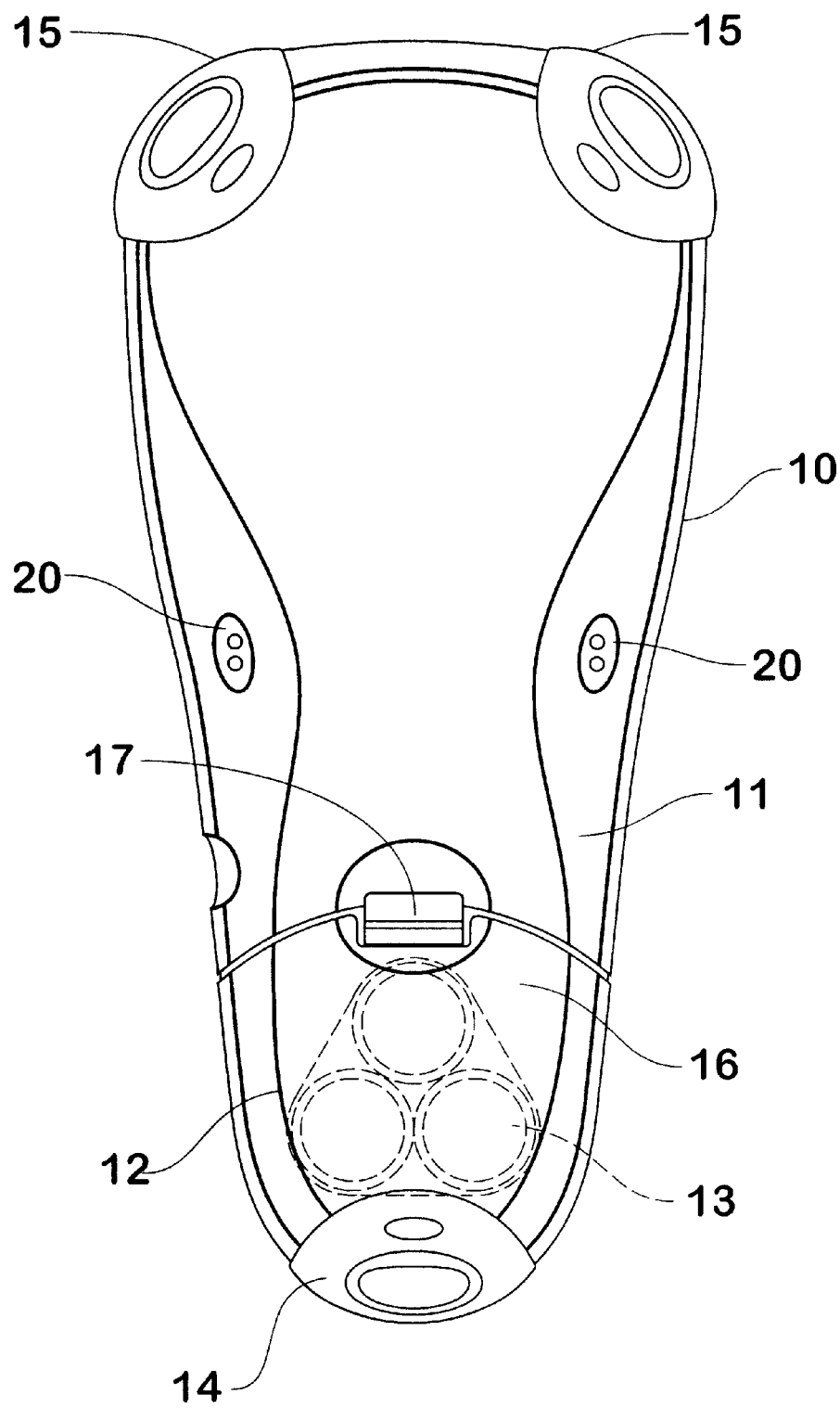
FIG. 11 is a plan view of the monitoring apparatus of FIG. 10, with top cover removed.
Figure 12:
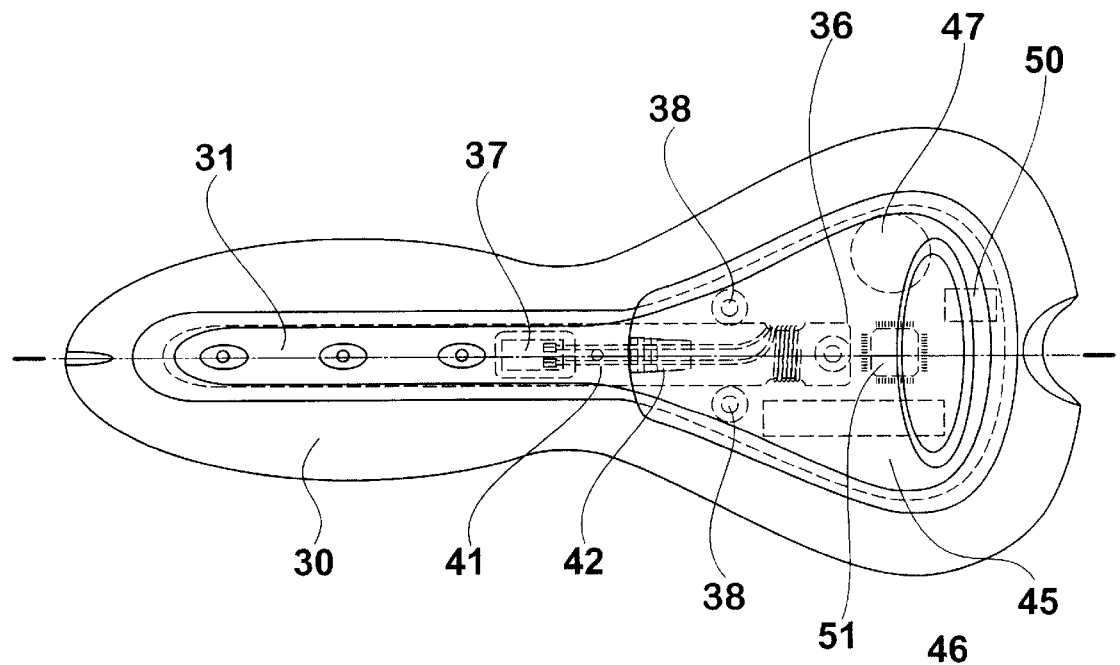
FIG. 12 is an exploded section view of the monitoring apparatus of FIGS. 10 and 11.
Figure 13:
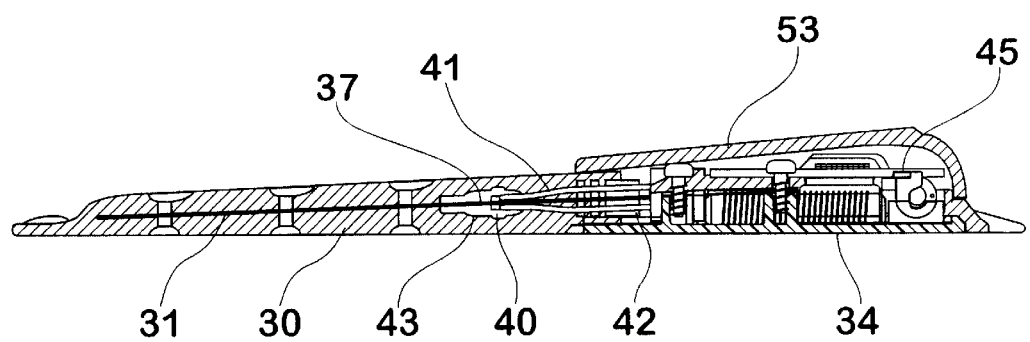
FIG. 13 is a plan view of the monitoring apparatus of FIGS. 10 to 12.
Figure 14:
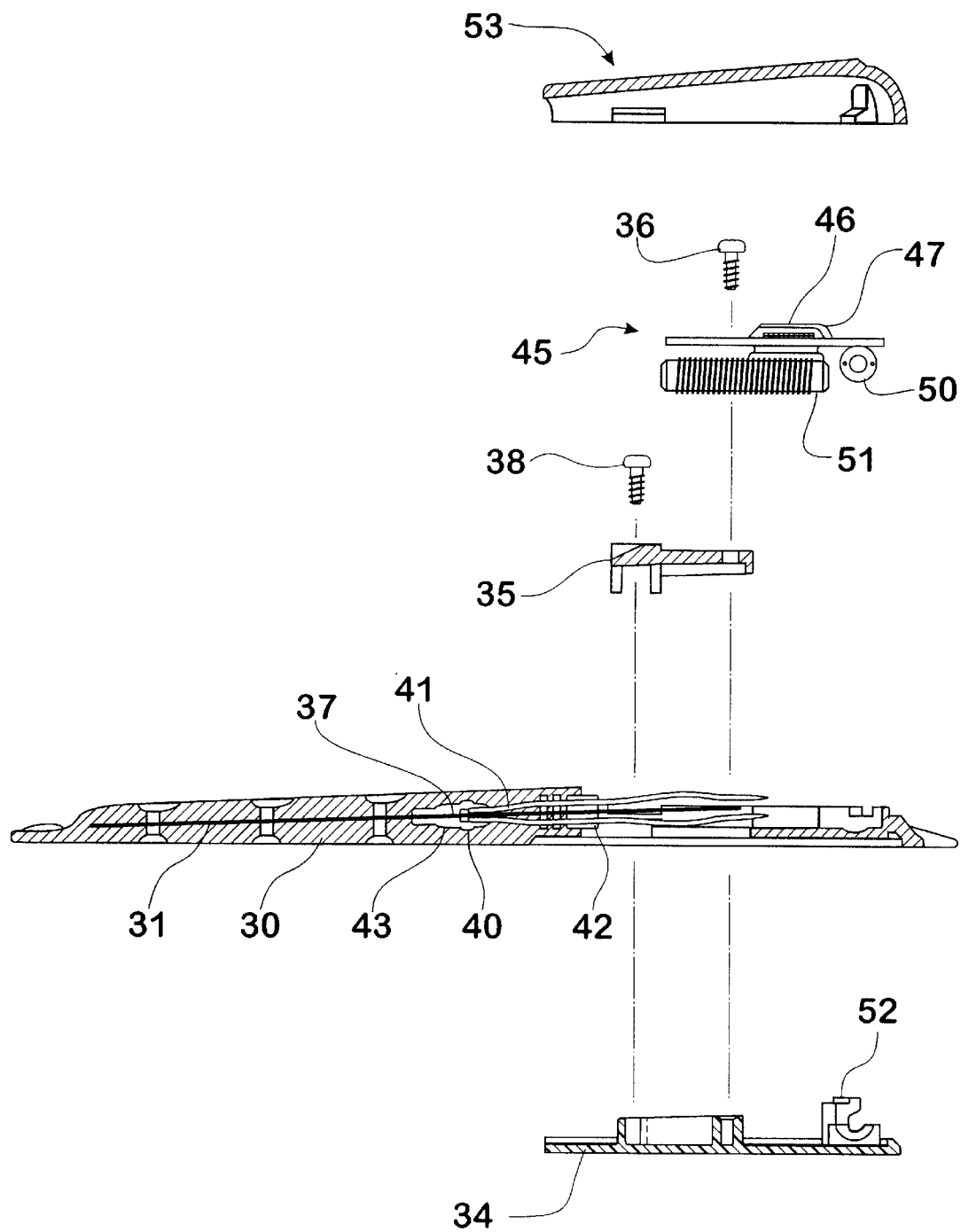
FIG. 14 is a side view of the monitoring apparatus of FIGS. 10 to 13.
Figure 15:
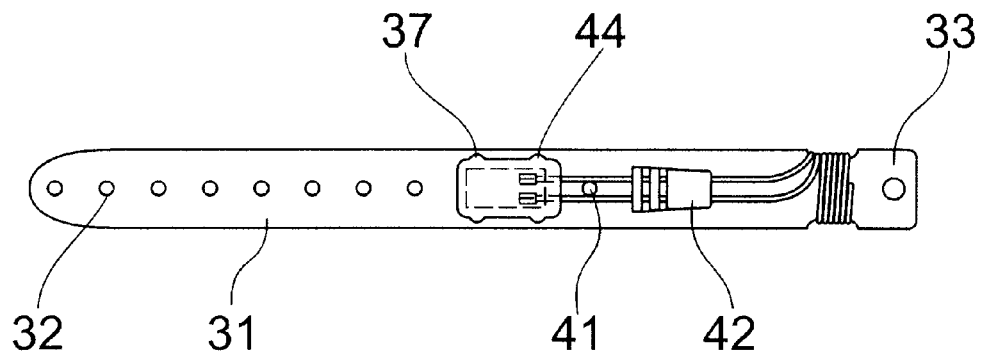
FIG. 15 is a side section view of the monitoring apparatus of FIGS. 10 to 14.
Figure 16:
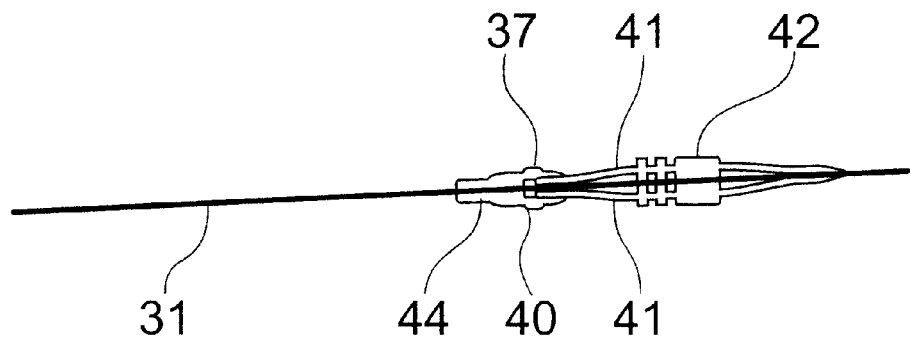
FIG. 16 is a side section detail view of the monitoring apparatus of FIGS. 10 to 15.

With reference to FIGS. 10 and 11, these are a front view and rear view of a console unit 10 in accordance with the present invention, wherein there is provided a moulded plastic case 11 having a battery compartment 12 provided at its lower rear portion and adapted to conceal three rechargeable NiMH batteries 13. Docking protection is provided by heel fitting 14, which is designed to complement corner protectors 15. The battery compartment 12 is covered by a moulded lid 16 secured by a latch 17. Facing the rear of the device and located at the sides are recharging and data ports 20. The front of the case 11 is provided with an aperture to receive a display assembly 21 which mounts an LCD display 22. The front face of the case 11 also includes apertures for three function keys 23 and a power key 24.

With reference to FIGS. 12 to 16, there is provided a monitoring apparatus unit comprising a moulded flexible body 30 substantially encapsulating a flexible stainless steel operating arm 31. The operating arm 31 is formed of 0.3 mm material and is provided with a plurality of apertures 32 for support during the moulding process and to allow the moulded material to migrate throughout the mould.

The rear end 33 is cantilevered from a substantially rigid base moulding 34 secured to the flexible body 30 at its rear portion. A printed circuit support 35 also functions to secure the operating arm 31 to the base moulding 34 by means of PC board mounting screw 36 and clamp screws 38 and form a cantilever chassis for the operating arm 31. The operating arm 31 is provided with a upper 37 and lower strain gauges bonded to the upper and lower faces respectively of the operating arm 31 at the point beyond the stiffening base moulding 34 to ensure that differential strain is experience on deflection of the operating arm 31.

Respective pairs of lead-in wires 41 lead from the strain gauges 37, 40 through respective moulded-in wire blocks 42 that are profiled to engage and be secured by the flexible body 30 during the moulding process. The material of the flexible body 30 is displaced at 43 to accommodate the strain gauges, which are encapsulated in a resin mass 44. The wire tails 41 are terminated as a PCB assembly 45 mounted to the printed circuit support 35, which assembly comprises a PC board bearing an LSI processor 46, rechargeable battery 47, vibrating motor and inductive coil 51. The PCB assembly 45 is secured against some vibration from the vibrating motor 50 in use by means of the motor being supported on a motor support 52 provided on the base moulding 34.

The inductive coil 51 is selected to fulfil the functions of transmitting and receiving element, and inductive power supply for charging the battery 47, under the control of the processor 46.

A top moulding 53 is provided with means to snap on over the base moulding 34 to enclose the PC board assembly 45, wherefore it may be ultrasonically welded in place to environment-proof the apparatus.

The base moulding 34 is in use intended to be located in the region of L4 and L5, the flexible body 30 and base moulding 34 being secured in place by surgical adhesive. Since the operating arm 31 is substantially flat before use, the first installation provides, a positive input from the strain gauges 37, 40 against which the apparatus may be calibrated to baseline.

Figure 17:
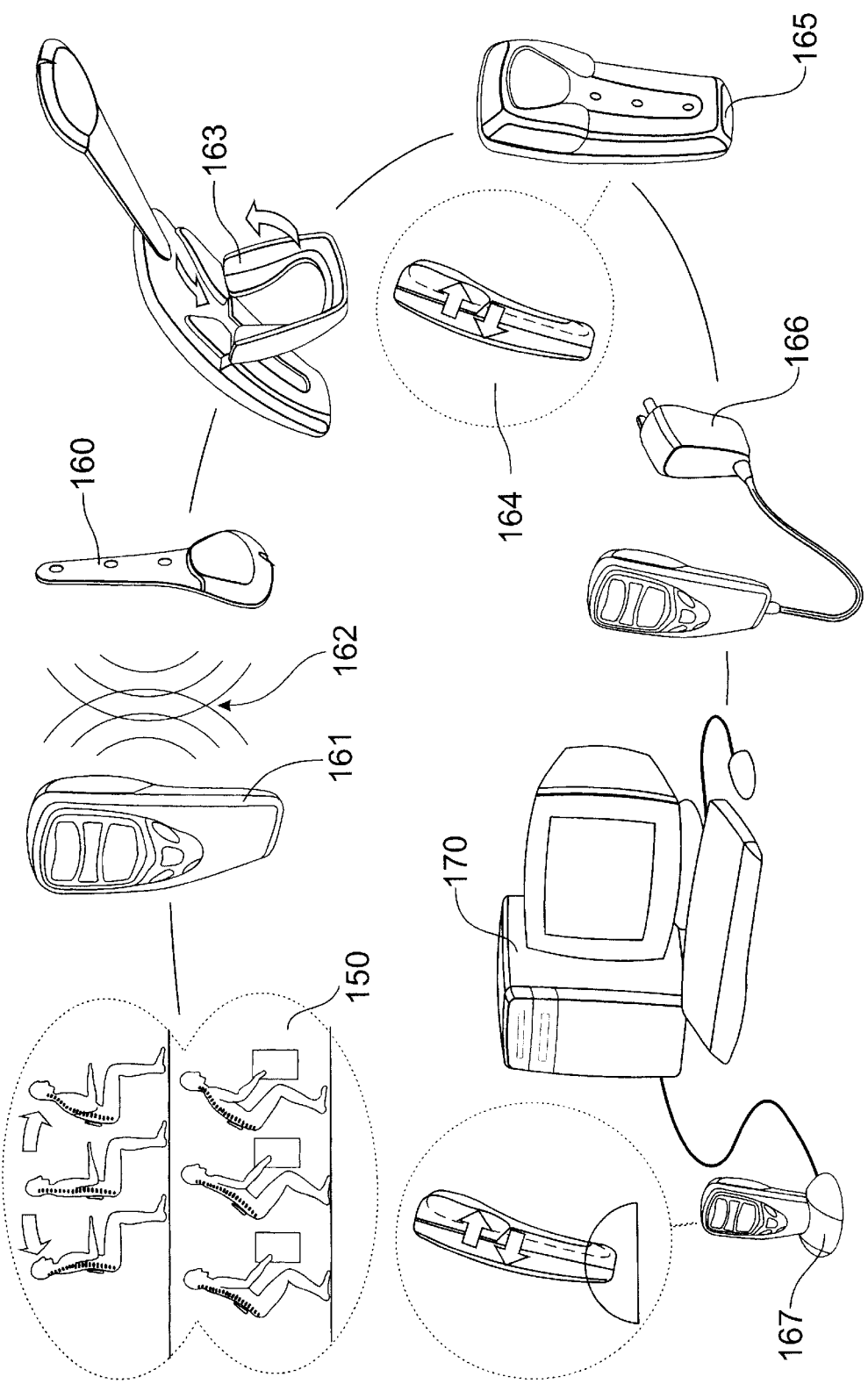
FIG. 17 is a representation of a single monitoring apparatus system in accordance with the present invention.

Operating modes of apparatus in accordance with the present invention are broadly described with reference to the illustrations of FIGS. 17 and 18, which in both cases illustrate the monitoring of a user 150 engaged in a variety of spinal configurations in sitting and lifting. In FIG. 17, a single monitoring apparatus 160 is paired to a single console 161. The monitoring apparatus 160 and console 161 are in communication via wireless waves 162 in use and for programming of the monitoring apparatus. The monitoring apparatus, when out of range of the console 161 operates in monitoring apparatus autonomous mode to continue the program. The console 161 is configured to receive the monitoring apparatus 160 for wireless charging of the monitoring apparatus 160 as well as being a convenient position for the monitoring apparatus for programming and stored data collection as at 164 as well as for transport and storage as at 165 A desk stand 163 is provided on the rear of the console 161. A charger 166 is supplied for the console 161, and by wireless therefrom to the monitoring apparatus 160. A data interface module 167 connects the console 161 to a PC 170 at the therapist's premises for base programming and data collection.

Figure 18:
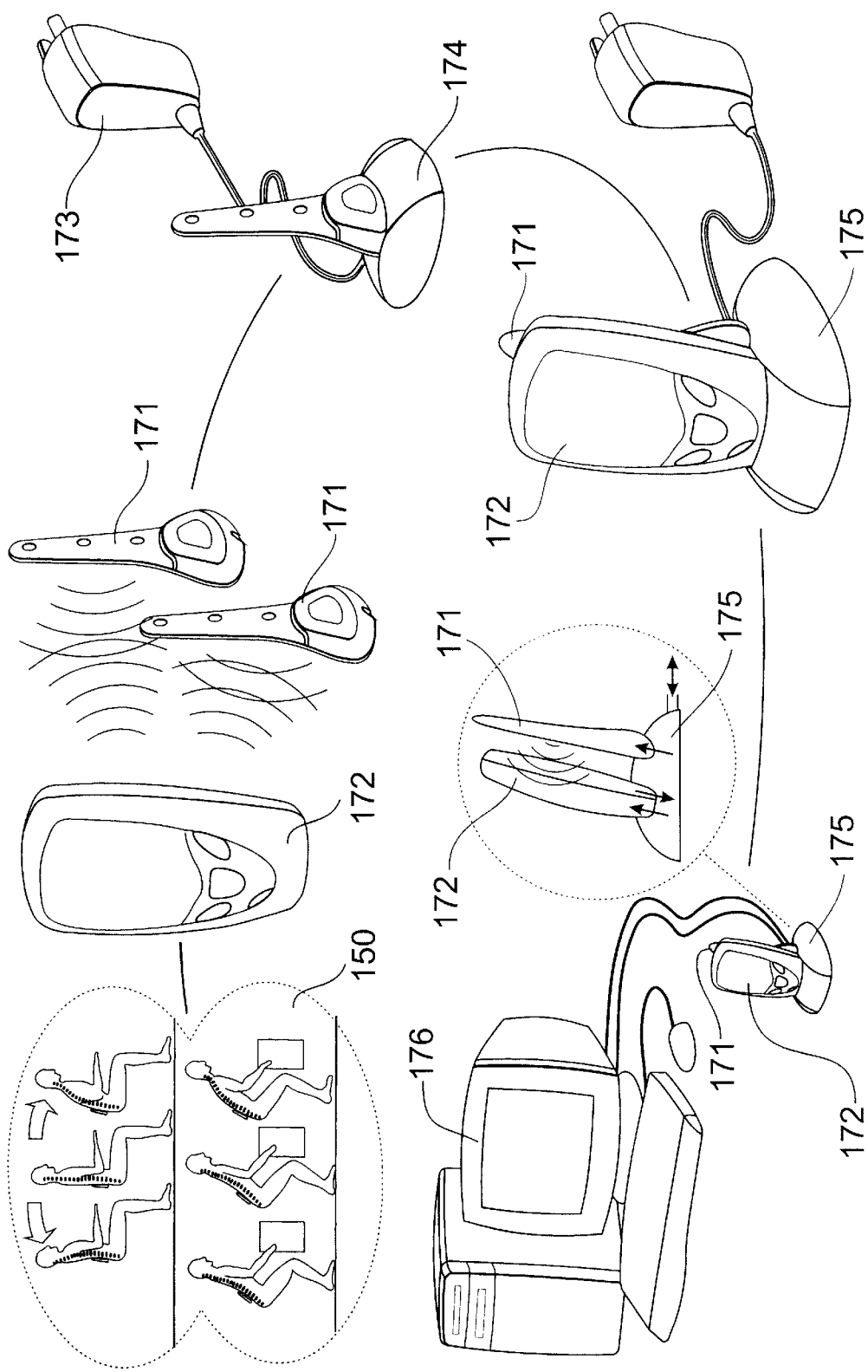
FIG. 18 is a representation of a multiple monitoring apparatus system in accordance with the present invention.
Figure 19:
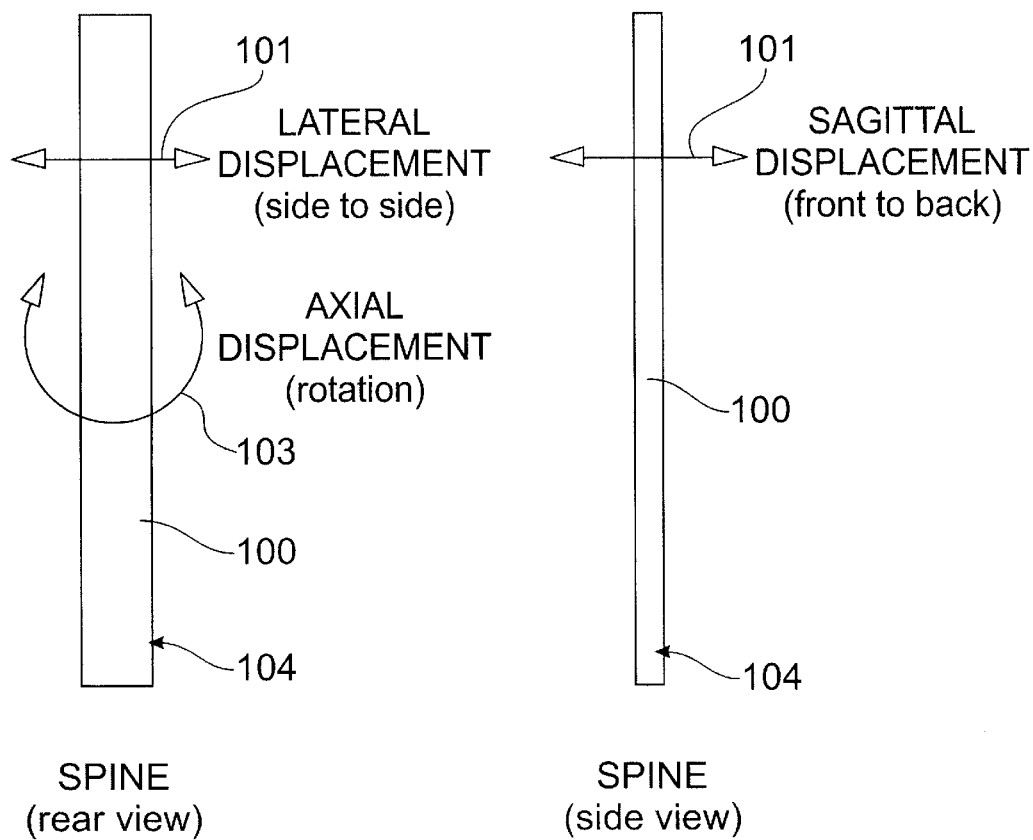
FIG. 19 is a diagram illustrating spinal movement modes.
Figures 20, 21:
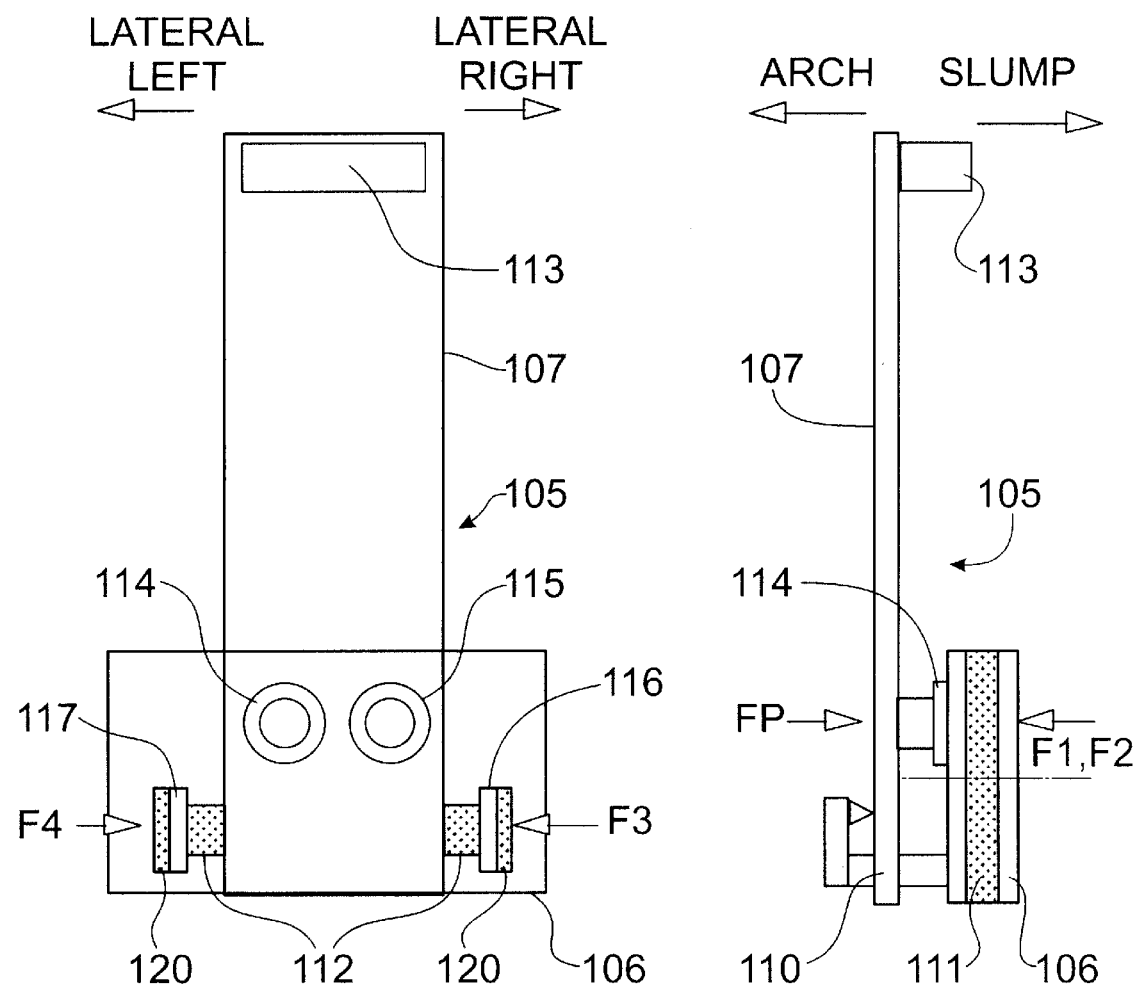
FIGS. 20 to 22 are plan, side and end views respectively of a monitoring apparatus arrangement suitable for use in monitoring multiple modes of spinal movement.
Figure 22:
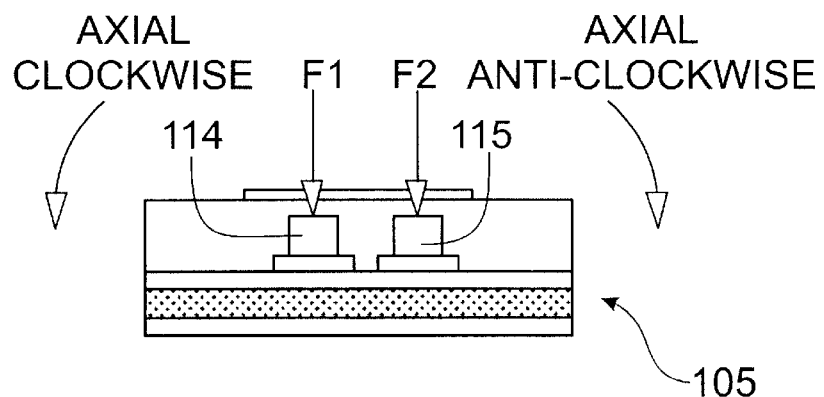

In the system illustrated in FIG. 18, multiple monitoring apparatus units 171 are associated with a single console 172 such as may be the case where a single therapist is monitoring several patients. The monitoring apparatus again communicate wirelessly with the console 172 when in-surgery and operate in monitoring apparatus autonomous mode when the patient leaves. The patient is provided with an individual charger 173 and desk stand 174 for home charging of the apparatus. The therapist is provided with a combined charger/data uptake module 175, wherein the console 172 and a monitoring apparatus 171 not with the patient may be charged, and whereby the apparatus may be configured, calibrated and/or analyzed by a PC.

Apparatus in accordance with the above described embodiment may also include a conditioned response feedback method to condition the muscles which stabilizes the spine thereby preventing or treating poor posture. Since no external or prosthetic physical support is provided, the apparatus makes the muscles provide the support for the spine thereby strengthening the muscles. The silent vibratory stimulus emitted by the apparatus onto the surface of the skin of the wearer is mildly unpleasant, thus reinforcing the conditioned response.

Accordingly, apparatus in accordance with the above embodiment does not simply encourage a straight back, but rather a fit and healthy back.

This particular embodiment was also provided with means to issue a vibration at selectable predetermined intervals, for example, every thirty (30) minutes in a distinct stimulus pattern as a reminder indicating that the wearer should bend and stretch gently and briefly to aid nutrition of the intervertebral discs. Alternatively, the apparatus may detect the period of postural monotony in lieu of the time base per se.

Apparatus of the abovedescribed kind is neither physically nor socially inhibiting since nothing can be seen or heard by others. It does not interfere with clothing and it allows the normal range of movement, for example, the wearer can bend over if necessary to tie shoelaces, pick up objects and the like.

In the alternative monitoring apparatus embodiment illustrated in FIGS. 19 to 22, FIG. 19 illustrates the different modes of spinal movement for which the alternative monitoring apparatus may be applied, wherein the spine 100 is symbolically represented in side view and rear view respectively. In the rear view, sideways displacements are termed lateral and are indicated by the arrow at 101. In the side view, movements from to back are termed sagittal and are indicated by the arrows 102. Rotations about the general spinal axis are termed axial and apply equally to both views, being indicated in the rear view by the arrows at 103. The displacements are relative to an arbitrary fixed point 104.

The monitoring apparatus unit if FIG. 3 is in these terms a sagittal plane monitoring apparatus. The embodiment of FIGS. 20 to 22 describes a monitoring apparatus enabling additional measurements to be made of axial and lateral displacements of the spine. In the figures there is provided a monitoring apparatus assembly 105 comprising a backing plate 106 adapted to be attached to the spinal vertebrae at L4 and L5 and mounting a flexible cantilever 107 via a transverse pivot 110, a resilient rotational coupling 111 and resilient lateral couplings 112. The cantilever 107 is adapted to be secured to the skin of the user at its outer end by an attachment point 113. The movement of the cantilever 107 about the pivot 110 in sagittal movement and about the resilient rotational coupling 111 causes the cantilever to interact with a pair of force sensors 114,115 with forces F1 and F2 respectively. The lateral movement results in displacement of the cantilever on the resilient lateral couplings 112, causing interaction with a pair of force sensors 116 and 117 with forces F3 and F4 respectively, the sensors 116 and 117 being mounted on respective supports 120 on the backing plate 106.

Measurement of the forces F1, F2, F3 and F4 enables sensible data to be obtained in respect of lateral, sagittal and axial motion of the spine as translated through the cantilever 107. The sagittal force Fs which is proportional to sagittal displacement may be expressed as:

$$Fs=(F1+F2)-Fp,$$

where Fp is a fixed preload force to ensure that the forces applies to the sensors 114 and 115 are always positive.

The axial force Fa which is proportional to the axial displacement of the spine may be expressed as:

$$Fa=(F1-F2),$$

where the sign of Fa determines whether the axial displacement of the spine is in the clockwise or anticlockwise direction. The differential forces applied to the sensors 114 and 115 arises out of torsional distortion of the resilient cantilever 107.

The lateral force Fl which is proportional to the lateral displacement of the spine may be expressed as:

$$Fl=(F4-F3),$$

where the sign of Fl determines lateral displacement of the spine to the left or right. Lateral spinal displacements result in rotation of the cantilever about the axis of the rotational coupling 111, causing a change in forces applied to the force sensors 116 and 117. The resilient couplings 112 are preloaded such that the force on the sensors 116 and 117 are always positive.

Whilst the first order equations above represent the dominant effects of the respective displacements on the sensors, in practice lower order effects will arise out of the complex interplay of characteristics of the cantilever, the rotational and flexible couplings, the flexibility of the user's skin and underlying tissues. Outputs varying from first order may be to some degree normalized by calibration.

Whilst apparatus is described with reference to the problems occurring in the lumbar region of the spine, the apparatus is in principle, equally applicable to the cervical and upper thoracic regions of the spine as well as in lateral curvature conditions such as scoliosis and rotations.

It is envisaged that the apparatus of the foregoing embodiments may be operable in various combinations and product specifications to accommodate differing technical requirements and markets. For convenience these are referred to as distinguishing marks. Mark I apparatus may comprise a paired monitoring apparatus and console set, wherein all interfacing with the monitoring apparatus is done via the console and the monitoring apparatus is otherwise keyless. A variation on the Mark I is the Mark II, wherein the console is provided with a PC interface.

A Mark III apparatus may comprise a stand-alone programmable monitoring apparatus, whereby each user of a set of multiple monitoring apparatus has no need for a console. The physiotherapist has a console which can individually program the set of monitoring apparatus such as the training range sensitivity (ie. curvature limits), set the training time dosage (eg. ten minutes), set the stimulus type (eg vibration and audio). The standalone programmable monitoring apparatus still has the ability to store data of the training sessions such as time, date, number of transgressions, type of transgression and the like The data is transferred to the console when the user returns to the physiotherapist for a progress check and/or treatment. The Mark III monitoring apparatus has one key to begin a posture training session and set the neutral or desired posture. The posture training sessions then operate according to the settings previously programmed into the monitoring apparatus by a console. The key if pressed and held down during a posture training session will end the session before the automatic cessation that otherwise would have occurred in accordance with the training time dosage.

A Mark IV apparatus may be described as a stand-alone, non programmable monitoring apparatus. The monitoring apparatus is a stand-alone product that does not communicate with other components and does not collect data. The settings that are variable on the Marks I to III are preset on the Mark IV. For example, the apparatus may be preconfigured to provide only vibratory stimulus or some other preconfigured stimulus, and the training dosage may be preset to, for example, five minutes or any other selected time. As a bare bones product, the Mark IV is the lowest cost option.

Mark V apparatus may comprise a cervical monitoring apparatus and as such may be of a Mark I to IV type.

It will of course be realised that while the foregoing has been given by way of illustrative example of this invention, all such and other modifications and variations thereto as would be apparent to persons skilled in the art are deemed to fall within the broad scope and ambit of this invention as defined in the claims appended hereto.

The claims defining the invention are as follows:

1. Apparatus for the prevention and treatment of posture deficiencies including:

monitoring means including a molded elastomeric body member having a bonding surface whereby the body member may be adhesively secured along a selected portion of a spine of a user and encapsulating an operating assembly comprising an elongate, resiliently flexible member cantilevered from a relatively rigid mounting portion located toward one end of said body member, said resiliently flexible member having mounted thereon a strain gauge in a region adjacent said mounting portion whereby strain in said resiliently flexible member produces a signal corresponding to curvature of a portion of the spine; and output means responsive to said signal and adapted to generate an output indicative of said curvature.

2. Apparatus for the prevention and treatment of posture deficiencies according to claim 1, wherein said selected portion of the spine is the lumbar portion.

3. Apparatus according to claim 2, wherein said body member comprises a unitary body member secured to the selected spinal portion and said strain gauge is responsive to a direct correspondence between the body member and the curvature of the spinal portion to which the body member is attached.

4. Apparatus for the prevention and treatment of posture deficiencies according to claim 1, wherein said monitoring means is configured such that mechanical reaction of the apparatus to movement of the spine of the user is minimized such that user awareness of the action of the apparatus is minimized.

5. Apparatus for the prevention and treatment of posture deficiencies according to claim 4, wherein said monitoring means contains discrete monitoring elements, and wherein interrelationship between adjacent elements is monitored by optical or electronic means and the signal generated is optical, electronic via an optical coupler, or electronic.

6. Apparatus for the prevention and treatment of posture deficiencies according to claim 1, wherein said signal interfaces with indicator means which is selected from one or more of vibratory stimuli, audio stimuli, electrical stimuli or a visual indication means.

7. Apparatus for the prevention and treatment of posture deficiencies according to claim 6, wherein said indicating means comprises an aversive indication of an adverse static or dynamic curvature to reinforce maintenance of good posture.

8. Apparatus for the prevention and treatment of posture deficiencies according to claim 7, wherein said aversive indication includes vibro-tactile stimulus of sub-audible frequency.

9. Apparatus for the prevention and treatment of posture deficiencies according to claim 6, wherein said indicator means is deactivatable to permit gathering of baseline data on a curvature function of the user independent of postural feedback.

10. Apparatus for the prevention and treatment of posture deficiencies according to claim 1, wherein said adhesive securing is by means selected from one or more of adhesive pads or tape members, adherable hook and loop fastenings, or straps.

11. Apparatus for the prevention and treatment of posture deficiencies according to claim 10, wherein said bonding surface is adapted to engage skin of the user by way of an adhesive layer.

12. Apparatus for the prevention and treatment of posture deficiencies according to claim 11, wherein said adhesive layer comprises a medical grade hypoallergenic adhesive.

13. Apparatus for the prevention and treatment of posture deficiencies according to claim 1, wherein said strain gauge is selected to provide a signal in response to the curvature of the spine as a consequence of the spine exceeding certain selected limits.

14. Apparatus for the prevention and treatment of posture deficiencies according to claim 1 wherein said monitoring means provides a continuous output across a range of positions of the monitoring means.

15. Apparatus for the prevention and treatment of posture deficiencies according to claim 14, wherein said elongated resiliently flexible member comprises a strip of metal or plastic embedded in the body member.

16. Apparatus for the prevention and treatment of posture deficiencies according to claim 15, wherein said monitoring means includes a pair of strain gauges mounted on opposite faces of said strip.

17. Apparatus for the prevention and treatment of posture deficiencies according to claim 16, wherein said strain gauges output data to means of recording condition status on a continuous, intermittent or condition responsive basis.

18. Apparatus for the prevention and treatment of posture deficiencies according to claim 17, wherein said strain gauges output data that is selectively used to trigger reacting means that serves to provide a condition responsive signal to the user.

19. Apparatus for the prevention and treatment of posture deficiencies according to claim 18 wherein the condition responsive signal is selected from immediate or selectably delayed stimulus.

20. Apparatus for the prevention and treatment of posture deficiencies according to claim 19, wherein both condition responsive and timed stimuli are supplied to the user, to indicate poor posture and to stimulate the user periodically for voluntary postural variety, respectively.

21. Apparatus for the prevention and treatment of posture deficiencies according to claim 20, wherein said strain gauges provide data to data collection means.

22. apparatus for the prevention and treatment of posture deficiencies according to claim 21, wherein said collection means includes one or more of a counter, time base record or the like adapted to record the number and timing of stimuli applied to the user.

23. Apparatus for monitoring the spinal posture of a person, comprising:

a substantially rigid support;

a resiliently flexible elongate member-having first and second opposed ends, said first end being mounted in cantilever fashion to the support;

at least one strain gauge mounted on the elongate member towards said first end, each strain gauge being responsive to strain in the elongate member to produce a signal indicative of the level of strain; and a flexible elastomeric body member encapsulating the support, the elongate member and the at least one strain gauge, and defining at least one major surface suitable for contacting a body of a user along a portion of the lumbar spine.

24. Apparatus according to claim 23, further including output means responsive to said signal to produce an output that is a measure of the spinal posture of the user.

25. Apparatus according to claim 23, wherein said at least one strain gauge comprises two strain gauges, the gauges being mounted on opposite faces of the elongate member towards said first end.

* * * * *